United States Patent
Buchanan et al.

(10) Patent No.: US 12,358,856 B1
(45) Date of Patent: Jul. 15, 2025

(54) COMPOSITIONS AND METHODS FOR THE PURIFICATION OF ISOPRENOIDS

(71) Applicant: Amyris, Inc., Emeryville, CA (US)

(72) Inventors: Greg Oniel Buchanan, Emeryville, CA (US); Wilson Chau, Emeryville, CA (US); Binita Bhattacharjee, Emeryville, CA (US); Anthony Spizuoco, Emeryville, CA (US); Liza Lopez, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 0 days.

(21) Appl. No.: 18/808,797

(22) Filed: Aug. 19, 2024

Related U.S. Application Data

(60) Provisional application No. 63/642,363, filed on May 3, 2024.

(51) Int. Cl.
*C07C 7/12* (2006.01)

(52) U.S. Cl.
CPC .................................. *C07C 7/12* (2013.01)

(58) Field of Classification Search
CPC ......................................................... C07C 7/12
See application file for complete search history.

(56) References Cited

U.S. PATENT DOCUMENTS

| | | | | |
|---|---|---|---|---|
| 3,538,179 A | * | 11/1970 | Nelson | C07C 7/1485 585/803 |
| 2017/0253885 A1 | * | 9/2017 | Jang | C12P 7/04 |

* cited by examiner

*Primary Examiner* — Thuan D Dang
(74) *Attorney, Agent, or Firm* — Clark & Elbing LLP

(57) ABSTRACT

The present disclosure provides compositions and methods for producing a high-purity isoprenoid from an isoprenoid composition, wherein the method includes using chromatography to reduce the impurities in the isoprenoid composition to below parts per million levels. Further provided herein are compositions containing high-purity isoprenoids.

24 Claims, 10 Drawing Sheets

FIG. 1

| Assay | Method | Specification | Result | Disposition |
|---|---|---|---|---|
| GC Purity | | ≥97.5%, wt% | 98.8 | Pass |
| Water by KF | | ≤ 100 mg/L | 19 | Pass |
| Total Acid Number | As described in Example 1 | ≤0.015 mg KOH/g | <0.01 | Pass |
| TBC by HPLC | | 30-100 mg/kg | 88 | Pass |
| Miscellaneous Sesquiterpenes | | < 1% *, area % | 0.59 | Pass |
| Oxygenated Hydrocarbon | | | | |
| Farnesol Isomers | | ≤ 75 mg/L ** | <LOQ^ | Pass |
| Farnesene Epoxide | | ≤ 22 mg/L ** | 8 | Pass |

* Sum of any single sesquiterpene < 1%
** Values are not mutually exclusive; must fit equation 75> [farnesol] (mg/L) +3.3*[fene epoxide] (mg/L)
^LOQ for the method described in Example 1 is 8 mg/L per individual analyte

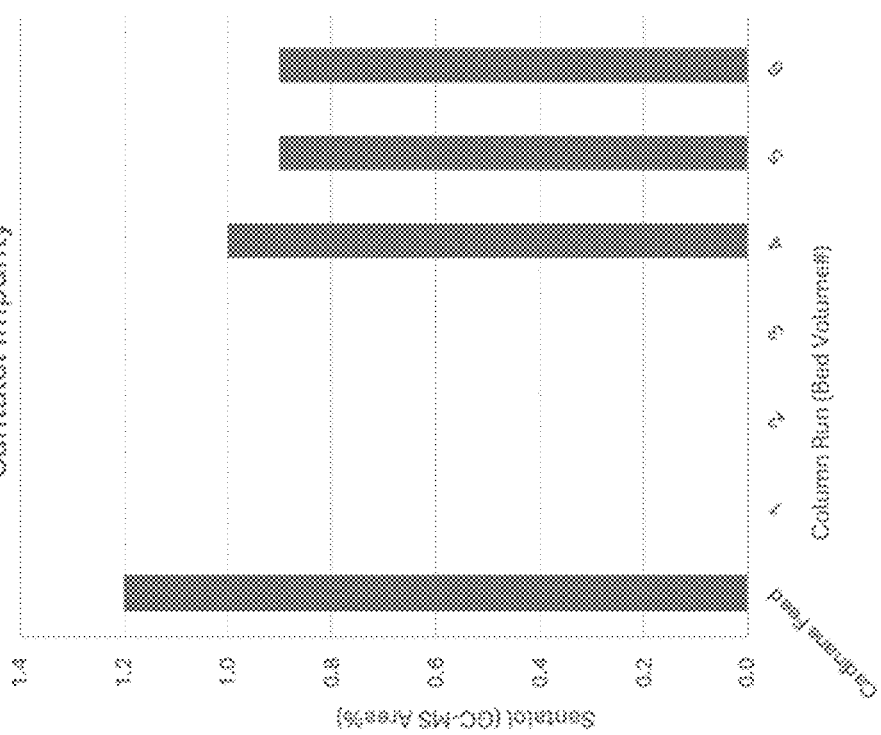

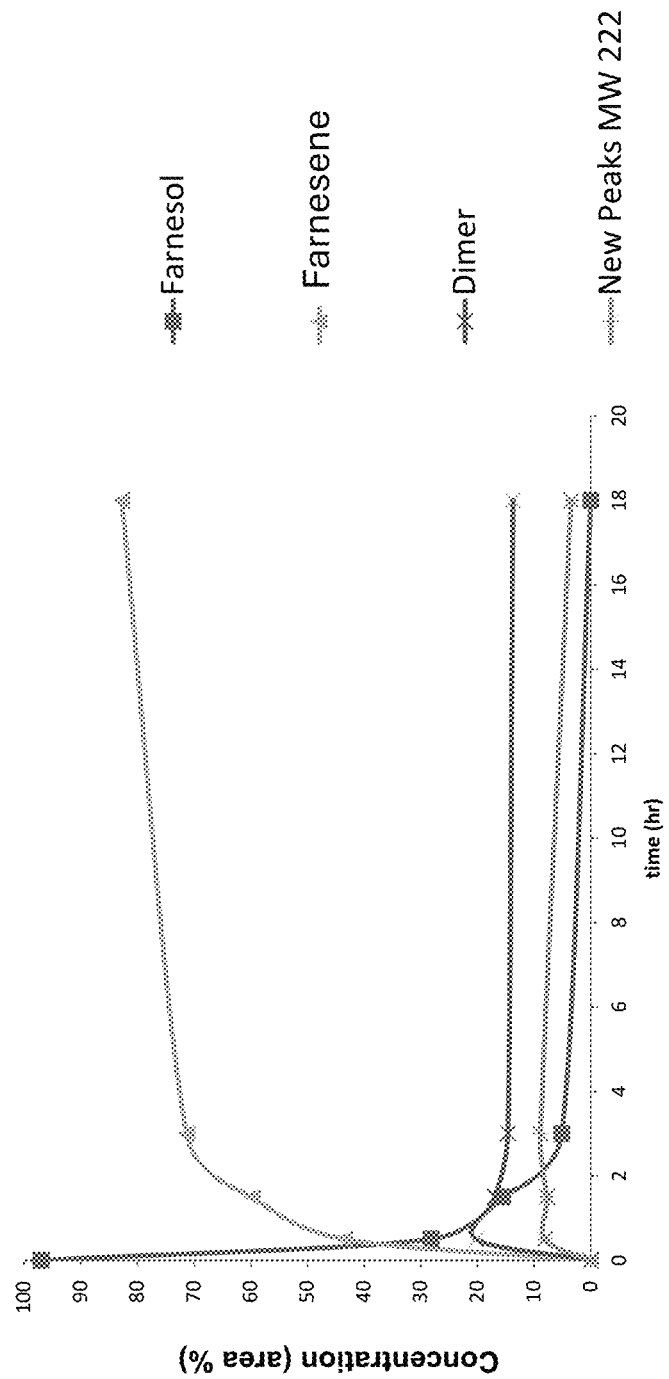

COMPOSITIONS AND METHODS FOR THE PURIFICATION OF ISOPRENOIDS

BACKGROUND OF THE INVENTION

Isoprenoids are ubiquitous in nature. They comprise a diverse family of over 40,000 individual molecules, many of which are vital to living organisms. Isoprenoids serve to maintain cellular fluidity, electron transport, and other metabolic functions. A vast number of natural and synthetic isoprenoids are useful as pharmaceuticals, cosmetics, perfumes, pigments and colorants, fungicides, antiseptics, nutraceuticals, and fine chemical intermediates. Given the large quantities of isoprenoid products needed for many commercial applications and the usefulness of isoprenoids as polymers, there remains a need for developing methods to produce isoprenoids.

Isoprenoids may be produced from a host cell and extracted then purified. In some cases, isoprenoids may be extracted and purified through processes such as centrifugation, distillation, and the like. The purified isoprenoids may have a purity of 95% (w/w) or above. However, certain impurities such as oxygenates may still need to be reduced to parts per million levels before the isoprenoid can be used in certain applications, for example, as a monomer in polymerization reactions. Therefore, there remains a need to develop methods for purifying isoprenoids with a purity suitable for applications such as polymerization reactions.

SUMMARY OF THE INVENTION

The present disclosure provides compositions and methods for isolating a high purity isoprenoid from an isoprenoid composition, as well as compositions of the high purity isoprenoid. The compositions and methods described herein address a problem that has been particularly challenging of how obtain isoprenoids from available sources (e.g., distilled isoprenoids) with sufficiently high purity such that the isoprenoid may be used in applications such as polymerization reactions, which are commercially valuable. Although isoprenoids can be produced using various methods, such as from host cells that express the enzymes involved in isoprenoid biosynthesis or by distilling isoprenoids from other sources, the resulting purity of the isoprenoids may not be high enough to effectively and consistently be used in applications such as polymerization reactions. Accordingly, in order to be able to use isoprenoids in applications such as polymerization reactions, the isoprenoid must be purified such that impurities are present at very low levels (e.g., parts per million). Given the extraordinarily high level of purity that is required, achieving such high purity isoprenoids presents significant difficulties.

The present disclosure is based, in part, on the surprising discovery that a unique combination of chromatography steps and treatment of resin described herein results in isoprenoid compositions having an extraordinarily high level of purity, which were not able to be achieved with other tested methods. The sections that follow provide a description of the compositions and methods that can be used to obtain a high purity isoprenoid from an isoprenoid composition.

In an aspect, the disclosure provides a method of purifying farnesene, the method comprising: (a) providing a farnesene composition; and (b) purifying the farnesene from the farnesene composition of (a) by way of chromatography.

In some embodiments, the farnesene composition comprises farnesene and one or more impurities. In some embodiments, the one or more impurities comprise one or more polar impurities. In some embodiments, the one or more polar impurities comprise farnesoic acid, farnesol, farnesene oxide, farnesene epoxide, a fatty acid, a sterol, HHFA, santalene, or santalol.

In some embodiments, the farnesene composition has a concentration of one or more impurities of between 1 ppm and 15,000 ppm (e.g., between 1 ppm and 10,000 ppm, 1 ppm and 5,000 ppm, 1 ppm and 1,0000 ppm, 1 ppm and 500 ppm, 1 ppm and 100 ppm, 100 ppm and 15,000 ppm, 1,000 ppm and 15,000 ppm, 5,000 ppm and 15,000 ppm, 10,000 ppm and 15,000 ppm, 5,000 ppm and 12,000 ppm, 1,000 ppm and 10,000 ppm, or 3,000 ppm and 14,000 ppm). In some embodiments, the farnesene composition has a concentration of one or more impurities of between 1000 ppm and 12,000 ppm (e.g., between 1000 ppm and 10,000 ppm, 1000 ppm and 8,000 ppm, 1000 ppm and 5,000 ppm, 1000 ppm and 2,000 ppm, 2,000 ppm and 12,000 ppm, 5,000 ppm and 12,000 ppm, 8,000 ppm and 12,000 ppm, 10,000 ppm and 12,000 ppm, 5,000 ppm to 10,000 ppm, or 3,000 ppm to 10,000 ppm). In some embodiments, the farnesene composition has a concentration of one or more impurities of between 100 ppm and 1,000 ppm (e.g., between 100 ppm and 800 ppm, 100 ppm and 600 ppm, 100 ppm and 400 ppm, 100 ppm and 200 ppm, 200 ppm and 1,000 ppm, 500 ppm and 1,000 ppm, 800 ppm and 1,000 ppm, or 300 ppm to 800 ppm).

In some embodiments, 4-tert butylcatechol is added to the farnesene composition. In some embodiments, the 4-tert butylcatechol is added to the farnesene composition to a concentration of from 50 ppm to 150 ppm (e.g., from 50 ppm to 125 ppm, 50 ppm to 100 ppm, 50 ppm to 75 ppm, 75 ppm to 150 ppm, 100 ppm to 150 ppm, 125 to 150 ppm, or 25 ppm to 75 ppm), optionally wherein the 4-tert butylcatechol is added to the farnesene composition to a concentration of about 100 ppm.

In some embodiments, the chromatography comprises: (a) pre-wetting a resin; (b) exposing the farnesene composition to the resin; and (c) collecting the farnesene from the resin. In some embodiments, the resin comprises aluminum oxide. In some embodiments, the aluminum oxide is basic aluminum oxide. In some embodiments, the aluminum oxide is acidic aluminum oxide. In some embodiments, the aluminum oxide is neutral aluminum oxide. In some embodiments, the resin comprises silica.

In some embodiments, the resin has a bulk density of between 0.1 g/mL and 0.75 g/mL (e.g., between 0.1 g/mL and 0.5 g/mL, 0.1 g/mL and 0.25 g/mL, 0.2 g/mL and 0.75 g/mL, 0.5 g/mL and 0.75 g/mL. 0. g/mL and 0.75 g/mL, or 0.3 g/mL and 0.5 g/mL). In some embodiments, the resin has a bulk density of between 0.25 g/mL and 0.5 g/mL (e.g., between 0.25 g/mL and 0.4 g/mL, 0.25 g/mL and 0.3 g/mL, 0.3 g/mL and 0.5 g/mL, 0.4 g/mL and 0.5 g/mL, or 0.3 g/mL and 0.4 g/mL). In some embodiments, the resin has a pore volume of between 0.1 mL/g and 1.5 mL/g (e.g., between 0.1 mL/g and 1.2 g/mL, 0.1 mL/g and 1 mL/g, 0.1 mL/g and 0.7 mL/g, 0.1 mL/g and 0.5 mL/g, 0.1 mL/g and 0.2 mL/g, 0.2 mL/g and 1.5 mL/g, 0.7 mL/g and 1.5 mL/g, 1 mL/g and 1.5 mL/g, 1.2 mL/g and 1.5 mL/g, or 0.5 mL/g and 1 mL/g). In some embodiments, the resin has a pore volume of between 0.5 mL/g and 1 mL/g (e.g., 0.5 mL/g, 0.6 mL/g, 0.7 mL/g, 0.8 mL/g, 0.9 mL/g, or 1 mL/g).

In some embodiments, the resin has a particle distribution size of between 25 μm and 800 μm (e.g., between 25 μm and 700 μm, 25 μm and 600 μm, 25 μm and 500 μm, 25 μm and 400 μm, 25 μm and 300 μm, 25 μm and 200 μm, 25 μm and 100 μm, 25 μm and 50 μm, 50 μm and 100 μm, 50 μm and 800 μm, 100 μm and 800 μm, 200 μm and 800 μm, 300 μm and 800 μm, 500 μm and 800 μm, 600 μm and 800 μm, or 50 μm and 200 μm). In some embodiments, the resin has a particle distribution size of between 100 μm and 800 μm (e.g., about 100 μm to about 700 μm, about 100 μm to about 600 μm, about 100 μm to about 500 μm, about 100 μm to about 400 μm, about 100 μm to about 300 μm, about 100 μm to about 200 μm, about 200 μm to about 800 μm, about 300 μm to about 800 μm, about 400 μm to about 800 μm, about 500 μm to about 800 μm, about 600 μm to about 800 μm, about 700 μm to about 800 μm, about 200 μm to about 600 μm). In some embodiments, the resin has a particle distribution size of between 300 μm and 600 μm (e.g., about 300 μm to about 550 μm, about 300 μm to about 500 μm, about 300 μm to about 450 μm, about 300 μm to about 400 μm, about 300 μm to about 350 μm, about 350 μm to about 600 μm, about 400 μm to about 600 μm, about 450 μm to about 600 μm, about 500 μm to about 600 μm, about 550 μm to about 600 μm, or about 400 μm and about 500 μm).

In some embodiments, the resin has an approximate water content of less than 1% w/w. In some embodiments, the resin has an approximate water content of between 0.01% w/w and 9% w/w (e.g., between 0.01% w/w to 1% w/w, 0.01% to 2% w/w, 0.1% w/w and 8% w/w, 0.1% w/w and 7% w/w, 0.1% w/w and 6% w/w, 0.1% w/w and 5% w/w, 0.1% w/w and 4% w/w, 0.1% w/w 3% w/w, 0.1% w/w and 2% w/w, 2% w/w and 6% w/w, 2% w/w and 5% w/w, 2% w/w and 4% w/w, 3% w/w and 9% w/w, 5% w/w and 9% w/w, 7% w/w and 9% w/w, or 4% w/w and 6% w/w). In some embodiments, the resin has an approximate water content of between 4.5% w/w to 6.5% w/w (e.g., between 4.5% w/w, 4.6% w/w, 4.7% w/w, 4.8% w/w, 4.9% w/w, 5% w/w, 5.1% w/w, 5.2% w/w, 5.3% w/w, 5.4% w/w, 5.5% w/w, 5.6% w/W, 5.7% w/w, 5.8% w/w, 5.9% w/w, 6% w/w, 6.1% w/w, 6.2% w/w, 6.3% w/w, 6.4% w/w, or 6.5% w/w).

In some embodiments, the pre-wetting step comprises fully wetting the resin by passing a solvent over the resin. In some embodiments, the pre-wetting step comprises passing the solvent over the resin in an amount of 1 bed volumes (BV) to 4 BV (e.g., 1 BV, 2 BV, 3 BV, or 4 BV). In some embodiments, the pre-wetting step comprises passing the solvent over the resin in an amount of 2 BV. In some embodiments, the solvent is passed over the resin with a minimum residence time on the column of at least 10 min in the pre-wetting step. In some embodiments, the solvent is passed over the resin with a maximum downflow superficial velocity of between 0.5 cm/min and 5 cm/min (e.g., between 0.5 cm/min and 5 cm/min, 1 cm/min and 5 cm/min, 2 cm/min and 5 cm/min, 3 cm/min and 5 cm/min, 4 cm/min and 5 cm/min, 0.5 cm/min and 4 cm/min, 0.5 cm/min and 2 cm/min, or 1 cm/min and 3 cm/min) in the pre-wetting step. In some embodiments, the solvent is passed over the resin with a maximum downflow superficial velocity of between 1 cm/min and 4 cm/min (e.g., between 1 cm/min and 3 cm/min, 1 cm/min and 2 cm/min, 2 cm/min and 4 cm/min, 3 cm/min and 4 cm/min, or 2 cm/min and 3 cm/min) in the pre-wetting step. In some embodiments, the solvent is passed over the resin with a maximum upflow superficial velocity of between 0.05 cm/min and 5 cm/min (e.g., between 0.5 cm/min and 5 cm/min, 1 cm/min and 5 cm/min, 2 cm/min and 5 cm/min, 3 cm/min and 5 cm/min, 4 cm/min and 5 cm/min, 0.5 cm/min and 4 cm/min, 0.5 cm/min and 2 cm/min, 1 cm/min and 3 cm/min, 0.05 cm/min and 3 cm/min, 0.05 cm/min and 1 cm/min, or 0.05 cm/min and 0.1 cm/min). In some embodiments, the solvent is passed over the resin with a maximum upflow superficial velocity of between 0.1 cm/min and 3 cm/min (e.g., between 1 cm/min and 3 cm/min, 1 cm/min and 2 cm/min, 0.1 cm/min and 2 cm/min, 0.1 cm/min and 1 cm/min, or 2 cm/min and 3 cm/min). In some embodiments, the pre-wetting step comprises fully wetting the resin with the farnesene composition.

In some embodiments, the farnesene composition is exposed to the resin following the pre-wetting step. In some embodiments, the farnesene composition is exposed to the resin that has not been subjected to a pre-wetting step comprising fully wetting the resin by passing a solvent over the resin. In some embodiments, the farnesene composition is exposed to the resin with a minimum residence time on the resin of at least 10 min. In some embodiments, the farnesene composition is exposed to the resin with a maximum downflow superficial velocity of between 1 cm/min and 15 cm/min (e.g., between 1 cm/min and 10 cm/min, 1 cm/min and 5 cm/min, 1 cm/min and 3 cm/min, 3 cm/min and 15 cm/min, 5 cm/min and 15 cm/min, 10 cm/min and 15 cm/min, or 5 cm/min and 10 cm/min). In some embodiments, the farnesene composition is exposed to the resin with a maximum downflow superficial velocity of between 5 cm/min and 11 cm/min (e.g., between 5 cm/min, 6 cm/min, 7 cm/min, 8 cm/min, 9 cm/min, 10 cm/min, or 11 cm/min). In some embodiments, the farnesene composition is exposed to the resin with a maximum upflow superficial velocity of between 0.1 cm/min and 10 cm/min (e.g., between 0.1 cm/min and 8 cm/min, 0.1 cm/min and 6 cm/min, 0.1 cm/min and 4 cm/min, 0.1 cm/min and 1 cm/min, 1 cm/min and 10 cm/min, 3 cm/min and 10 cm/min, 5 cm/min and 10 cm/min, 8 cm/min and 10 cm/min, 4 cm/min and 8 cm/min, or 2 cm/min and 6 cm/min). In some embodiments, the farnesene composition is exposed to the resin with a maximum upflow superficial velocity of between 1 cm/min and 5 cm/min (e.g., between 1 cm/min, 2 cm/min, 3 cm/min, 4 cm/min, or 5 cm/min). In some embodiments, the steps (a) through (c) are repeated from 2 to 20 times (e.g., 2, 3, 4, 5, 6, 7, 8, 9, 10, 11, 12, 13, 14, 15, 16, 17, 18, 19, or 20 times). The flow rate may be adjusted to result in an isoprenoid product of higher purity relative to a different flow rate. For example, the flow rate may be reduced to result in an isoprenoid product having greater purity compared to when a higher flow rate is used. In some embodiments, the steps (a) through (c) are repeated from 2 to 10 times (e.g., 2, 3, 4, 5, 6, 7, 8, 9, or 10 times). In some embodiments, the steps (a) through (c) are repeated 6 times. In some embodiments, the steps (a) through (c) are repeated from 2 to 4 times (e.g., 2, 3, or 4 times).

In some embodiments, the resin is regenerated following the collection of the farnesene from the resin in step (c). In some embodiments, the resin is regenerated by: (a) adding a polar solvent to the resin; (b) removing the polar solvent from the resin; (c) heating the resin; and (d) cooling the resin. In some embodiments, step (a) is performed by adding polar solvent to the resin in an amount of between 1 BV and 10 BV (e.g., 1 BV, 2 BV, 3 BV, 4 BV, 5 BV, 6 BV, 7 BV, 8 BV, 9 BV, or 10 BV). In some embodiments, the polar solvent is added to the resin in an amount of between 2 BV and 6 BV (e.g., 1 BV, 2 BV, 3 BV, 4 BV, 5 BV, or 6 BV). In some embodiments, the polar solvent is added to the resin in an amount of about 4 BV. In some embodiments, step (c) is performed by heating the resin to a temperature of between 100° C. and 200° C. (e.g., between 100° C. and 180° C., 100° C. and 160° C., 100° C. and 140° C., 100° C. and 120° C., 120° C. and 200° C., 150° C. and 200° C., 170° C. and 200° C., 140° C. and 180° C., or 120° C. and 160° C.). In some embodiments, the resin is heated to a temperature of about 150° C. In some embodiments, the polar solvent is methanol. In some embodiments, the polar solvent is isopropanol. In some embodiments, the cooling of step (d) is performed by cooling the resin to room temperature. In some embodiments, the chromatography is performed under $N_2$.

In some embodiments, the farnesene is purified from the farnesene composition with a purity of from about 95% (w/w) to about 100% (w/w) (e.g., 95% (w/w) to 100% (w/w) or more, e.g., 95% (w/w), 95.5% (w/w), 96% (w/w), 96.5% (w/w), 97% (w/w), 97.5% (w/w), 98% (w/w), 98.5% (w/w), 99% (w/w), 99.5% (w/w) or 100% (w/w), or more). In some embodiments, the farnesene is purified from the farnesene composition with a purity of from about 98% (w/w) to about 100% (w/w) (e.g., 98% (w/w), 98.1% (w/w), 98.2 wt, 98.3% (w/w), 98.4% (w/w), 98.5% (w/w), 98.6% (w/w), 98.7% (w/w), 98.8% (w/w), 98.9% (w/w), 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). In some embodiments, the farnesene is purified from the farnesene composition with a purity of from about 99% (w/w) to about 100% (w/w) (e.g., 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). In some embodiments, the is purified from the farnesene composition with a purity of is from about 99.5% (w/w) to about 100% (w/w) (e.g., 99.5% (w/w), 99.6% (w/w), 99.7% (w/w), 99.8% (w/w), 99.9% (w/w), or 100% (w/w)).

In an aspect, the disclosure provides a composition comprising farnesene, wherein the composition is produced by any one of the methods described herein. In some embodiments, the farnesene has a purity of from about 95% (w/w) to about 100% (w/w) (e.g., 95% (w/w) to 100% (w/w) or more, e.g., 95% (w/w), 95.5% (w/w), 96% (w/w), 96.5% (w/w), 97% (w/w), 97.5% (w/w), 98% (w/w), 98.5% (w/w), 99% (w/w), 99.5% (w/w) or 100% (w/w), or more). In some embodiments, the farnesene has a purity of from about 98% (w/w) to about 100% (w/w)) (e.g., 98% (w/w), 98.1% (w/w), 98.2 wt, 98.3% (w/w), 98.4% (w/w), 98.5% (w/w), 98.6% (w/w), 98.7% (w/w), 98.8% (w/w), 98.9% (w/w), 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)), optionally wherein the farnesene has a purity of from about 99% (w/w) to about 100% (w/w) (e.g., 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). In some embodiments, the farnesene has a purity of from about 99.5% (w/w) to about 100% (w/w) (e.g., 99.5% (w/w), 99.6% (w/w), 99.7% (w/w), 99.8% (w/w), 99.9% (w/w), or 100% (w/w)). In some embodiments, the composition comprises one or more impurities comprising farnesoic acid, farnesol, farnesene oxide, farnesene epoxide, a fatty acid, a sterol, HHFA, santalene, or santalol.

In an aspect, the disclosure provides a composition comprising farnesene and one or more impurities, wherein the purity of the farnesene is from about 95% (w/w) to about 100% (w/w) (e.g., 95% (w/w) to 100% (w/w) or more, e.g., 95% (w/w), 95.5% (w/w), 96% (w/w), 96.5% (w/w), 97% (w/w), 97.5% (w/w), 98% (w/w), 98.5% (w/w), 99% (w/w), 99.5% (w/w) or 100% (w/w), or more), and wherein the one or more impurities comprise farnesoic acid, farnesol, farnesene oxide, farnesene epoxide, a fatty acid, a sterol, HHFA, santalene, or santalol.

In some embodiments, the composition comprises farnesol having a concentration of farnesol is between 0 mg/mL and 1 g/L (e.g., between 0.2 g/L and 1 g/L, 0.4 g/L and 1 g/L, 0.6 g/L and 1 g/L, 0.8 g/L and 1 g/L, 0 mg/mL, and 0.8 g/L, 0 mg/ml and 0.6 g/L, 0 mg/mL and 0.4 g/L, 0 mg/mL and 0.2 g/L, 0.4 g/L and 0.6 g/L, or 0.2 g/L and 0.8 g/L).

In some embodiments, the concentration of farnesol is between 0 mg/L and 600 mg/L (e.g., between 0 mg/ml and 500 mg/mL, 0 mg/mL and 400 mg/mL, 0 mg/mL and 300 mg/mL, 0 mg/mL and 200 mg/mL, 0 mg/mL and 100 mg/mL, 100 mg/mL and 600 mg/mL, 200 mg/mL and 600 mg/mL, 300 mg/ml and 600 mg/mL, 400 mg/ml and 600 mg/mL, 500 mg/mL and 600 mg/mL, 200 mg/mL and 400 mg/mL, or 300 mg/mL and 500 mg/mL). In some embodiments, the concentration of farnesol is less than 500 mg/L.

In some embodiments, the composition comprises farnesene epoxide having a concentration of farnesol is between 0 mg/mL and 500 mg/L (e.g., between 0 mg/ml and 400 mg/mL, 0 mg/mL and 300 mg/mL, 0 mg/mL and 200 mg/mL, 0 mg/ml and 100 mg/mL, 100 mg/mL and 500 mg/mL, 200 mg/mL and 500 mg/mL, 300 mg/mL and 500 mg/mL, 400 mg/mL and 500 mg/mL, 200 mg/mL and 400 mg/mL, or 100 mg/mL and 300 mg/mL). In some embodiments, the concentration of farnesene epoxide is between 0 mg/L and 200 mg/L (e.g., between 0 mg/L and 150 mg/L, 0 mg/L and 100 mg/L, 0 mg/L and 50 mg/L, 50 mg/L and 200 mg/L, 100 mg/L and 200 mg/L, 150 mg/L and 200 mg/L, 20 mg/L and 100 mg/L, or 50 mg/L and 150 mg/L). In some embodiments, the concentration of farnesene epoxide is less than 150 mg/L.

In an aspect, the disclosure provides a composition comprising farnesene and one or more carriers, diluents, or excipients, wherein the purity of the farnesene is from about 99.5% (w/w) to about 100% (w/w) (e.g., 99.5% (w/w), 99.6% (w/w), 99.7% (w/w), 99.8% (w/w), 99.9% (w/w), or 100% (w/w)).

In some embodiments, the farnesene is present with one or more impurities, and wherein the one or more impurities is present in a concentration of about 0.5% (w/w) or less.

In some embodiments, the one or more impurities is present in a concentration of about 0.4% (w/w) or less. In some embodiments, the one or more impurities is present in a concentration of about 0.3% (w/w) or less. In some embodiments, the one or more impurities is present in a concentration of about 0.2% (w/w) or less. In some embodiments, the one or more impurities is present in a concentration of about 0.1% (w/w) or less.

In some embodiments, the one or more impurities comprise farnesoic acid, farnesol, farnesene oxide, farnesene epoxide, a fatty acid, a sterol, HHFA, santalene, or santalol.

In an aspect the disclosure provides a method of purifying isoprenoid comprising: (a) providing an isoprenoid composition; and (b) purifying the isoprenoid from the isoprenoid composition of (a) by way of chromatography. In some embodiments, the isoprenoid composition comprises an isoprenoid and one or more impurities. In some embodiments, the one or more impurities comprise one or more polar impurities. In some embodiments, the one or more polar impurities comprise farnesoic acid, farnesol, farnesene oxide, farnesene epoxide, a fatty acid, a sterol, HHFA, santalene, or santalol. In some embodiments, the isoprenoid composition has a concentration of one or more impurities of between 1 ppm and 15,000 ppm (e.g., between 1 ppm and 10,000 ppm, 1 ppm and 5,000 ppm, 1 ppm and 1,0000 ppm, 1 ppm and 500 ppm, 1 ppm and 100 ppm, 100 ppm and 15,000 ppm, 1,000 ppm and 15,000 ppm, 5,000 ppm and 15,000 ppm, 10,000 ppm and 15,000 ppm, 5,000 ppm and 12,000 ppm, 1,000 ppm and 10,000 ppm, or 3,000 ppm and 14,000 ppm). In some embodiments, the isoprenoid composition has a concentration of one or more impurities of between 1000 ppm and 12,000 ppm (e.g., between 1000 ppm and 10,000 ppm, 1000 ppm and 8,000 ppm, 1000 ppm and 5,000 ppm, 1000 ppm and 2,000 ppm, 2,000 ppm and 12,000 ppm, 5,000 ppm and 12,000 ppm, 8,000 ppm and 12,000 ppm, 10,000 ppm and 12,000 ppm, 5,000 ppm to 10,000 ppm, or 3,000 ppm to 10,000 ppm). In some embodiments, the isoprenoid composition has a concentration of one or more impurities of between 100 ppm and 1,000 ppm.

In some embodiments, 4-tert butylcatechol is added to the isoprenoid composition. In some embodiments, the 4-tert butylcatechol is added to the isoprenoid composition to a concentration of from 50 ppm to 150 ppm (e.g., from 50 ppm to 125 ppm, 50 ppm to 100 ppm, 50 ppm to 75 ppm, 75 ppm to 150 ppm, 100 ppm to 150 ppm, 125 to 150 ppm, or 25 ppm to 75 ppm), optionally wherein the 4-tert butylcatechol is added to the isoprenoid composition to a concentration of about 100 ppm. In some embodiments, the chromatography comprises: (a) pre-wetting a resin; (b) exposing the isoprenoid composition to the resin; and (c) collecting the isoprenoid from the resin. In some embodiments, the resin comprises aluminum oxide. In some embodiments, the aluminum oxide is basic aluminum oxide. In some embodiments, the aluminum oxide is acidic aluminum oxide. In some embodiments, the aluminum oxide is neutral aluminum oxide. In some embodiments, the resin comprises silica. In some embodiments, the resin has a bulk density of between 0.1 g/mL and 0.75 g/mL (e.g., between 0.1 g/mL and 0.5 g/mL, 0.1 g/mL and 0.25 g/mL, 0.2 g/mL and 0.75 g/mL, 0.5 g/mL and 0.75 g/mL. 0. g/mL and 0.75 g/mL, or 0.3 g/mL and 0.5 g/mL). In some embodiments, the resin has a bulk density of between 0.25 g/mL and 0.5 g/mL (e.g., between 0.25 g/mL and 0.4 g/mL, 0.25 g/mL and 0.3 g/mL, 0.3 g/mL and 0.5 g/mL, 0.4 g/mL and 0.5 g/mL, or 0.3 g/mL and 0.4 g/mL). In some embodiments, the resin has a pore volume of between 0.1 mL/g and 1.5 mL/g (e.g., between 0.1 mL/g and 1.2 g/mL, 0.1 mL/g and 1 mL/g, 0.1 mL/g and 0.7 mL/g, 0.1 mL/g and 0.5 mL/g, 0.1 mL/g and 0.2 mL/g, 0.2 mL/g and 1.5 mL/g, 0.7 mL/g and 1.5 mL/g, 1 mL/g and 1.5 mL/g, 1.2 mL/g and 1.5 mL/g, or 0.5 mL/g and 1 mL/g). In some embodiments, the resin has a pore volume of between 0.5 mL/g and 1 mL/g (e.g., 0.5 mL/g, 0.6 mL/g, 0.7 mL/g, 0.8 mL/g, 0.9 mL/g, or 1 mL/g).

In some embodiments, the resin has a particle distribution size of between 25 μm and 800 μm (e.g., between 25 μm and 700 μm, 25 μm and 600 μm, 25 μm and 500 μm, 25 μm and 400 μm, 25 μm and 300 μm, 25 μm and 200 μm, 25 μm and 100 μm, 25 μm and 50 μm, 50 μm and 100 μm, 50 μm and 800 μm, 100 μm and 800 μm, 200 μm and 800 μm, 300 μm and 800 μm, 500 μm and 800 μm, 600 μm and 800 μm, or 50 μm and 200 μm). In some embodiments, the resin has a particle distribution size of between 100 μm and 800 μm (e.g., about 100 μm to about 700 μm, about 100 μm to about 600 μm, about 100 μm to about 500 μm, about 100 μm to about 400 μm, about 100 μm to about 300 μm, about 100 μm to about 200 μm, about 200 μm to about 800 μm, about 300 μm to about 800 μm, about 400 μm to about 800 μm, about 500 μm to about 800 μm, about 600 μm to about 800 μm, about 700 μm to about 800 μm, about 200 μm to about 600 μm). In some embodiments, the resin has a particle distribution size of between 300 μm and 600 μm (e.g., about 300 μm to about 550 μm, about 300 μm to about 500 μm, about 300 μm to about 450 μm, about 300 μm to about 400 μm, about 300 μm to about 350 μm, about 350 μm to about 600 μm, about 400 μm to about 600 μm, about 450 μm to about 600 μm, about 500 μm to about 600 μm, about 550 μm to about 600 μm, or about 400 μm and about 500 μm). In some embodiments, the resin has an approximate water content of less than 0.01% w/w. In some embodiments, the resin has an approximate water content of between 0.01% (w/w) and 9% (w/w) (e.g., between 0.01% w/w and 1% w/W, 0.01% w/w and 2% w/w, 0.1% w/w and 8% w/w, 0.1% w/w and 7% w/w, 0.1% w/w and 6% w/w, 0.1% w/w and 5% w/w, 0.1% w/w and 4% w/w, 0.1% w/w 3% w/w, 0.1% w/w and 2% w/w, 2% w/w and 6% w/w, 2% w/w and 5% w/w, 2% w/w and 4% w/w, 3% w/w and 9% w/w, 5% w/w and 9% w/w, 7% w/w and 9% w/w, or 4% w/w and 6% w/w). In some embodiments, the resin has an approximate water content of between 4.5% (w/w) to 6.5% (w/w) (e.g., 4.5% w/w, 4.6% w/w, 4.7% w/w, 4.8% w/w, 4.9% w/w, 5% w/w, 5.1% w/w, 5.2% w/w, 5.3% w/w, 5.4% w/w, 5.5% w/w, 5.6% w/w, 5.7% w/w, 5.8% w/w, 5.9% w/w, 6% w/W, 6.1% w/w, 6.2% w/w, 6.3% w/w, 6.4% w/w, or 6.5% w/w).

In some embodiments, the pre-wetting step comprises fully wetting the resin by passing a solvent over the resin. In some embodiments, the pre-wetting step comprises passing the solvent over the resin in an amount of 1 BV to 4 BV (e.g., 1 BV, 2 BV, 3 BV, or 4 BV). In some embodiments, the pre-wetting step comprises passing the solvent over the resin in an amount of 2 BV. In some embodiments, the solvent is passed over the resin with a minimum residence time on the column of at least 10 min in the pre-wetting step. In some embodiments, the solvent is passed over the resin with a maximum downflow superficial velocity of between 0.5 cm/min and 5 cm/min (e.g., between 0.5 cm/min and 5 cm/min, 1 cm/min and 5 cm/min, 2 cm/min and 5 cm/min, 3 cm/min and 5 cm/min, 4 cm/min and 5 cm/min, 0.5 cm/min and 4 cm/min, 0.5 cm/min and 2 cm/min, or 1 cm/min and 3 cm/min) in the pre-wetting step. In some embodiments, the solvent is passed over the resin with a maximum downflow superficial velocity of between 1 cm/min and 4 cm/min (e.g., between 1 cm/min and 3 cm/min, 1 cm/min and 2 cm/min, 2 cm/min and 4 cm/min, 3 cm/min and 4 cm/min, or 2 cm/min and 3 cm/min) in the pre-wetting step. In some embodiments, the solvent is passed over the resin with a maximum upflow superficial velocity of between 0.05 cm/min and 5 cm/min (e.g., between 0.5 cm/min and 5 cm/min, 1 cm/min and 5 cm/min, 2 cm/min and 5 cm/min, 3 cm/min and 5 cm/min, 4 cm/min and 5 cm/min, 0.5 cm/min and 4 cm/min, 0.5 cm/min and 2 cm/min, 1 cm/min and 3 cm/min, 0.05 cm/min and 5 cm/min, 0.05 cm/min and 1 cm/min, or 0.05 cm/min and 0.1 cm/min). In some embodiments, the solvent is passed over the resin with a maximum upflow superficial velocity of between 0.1 cm/min and 3 cm/min (e.g., between 1 cm/min and 3 cm/min, 1 cm/min and 2 cm/min, 0.1 cm/min and 2 cm/min, 0.1 cm/min and 1 cm/min, or 2 cm/min and 3 cm/min). In some embodiments, the pre-wetting step comprises fully wetting the resin with the isoprenoid composition.

In some embodiments, the isoprenoid composition is exposed to the resin following the pre-wetting step. In some embodiments, the isoprenoid composition is exposed to the resin that has not been subjected to a pre-wetting step comprising fully wetting the resin by passing a solvent over the resin. In some embodiments, the isoprenoid composition is exposed to the resin with a minimum residence time on the resin of at least 10 min. In some embodiments, the isoprenoid composition is exposed to the resin with a maximum downflow superficial velocity of between 1 cm/min and 15 cm/min (e.g., between 1 cm/min and 10 cm/min, 1 cm/min and 5 cm/min, 1 cm/min and 3 cm/min, 3 cm/min and 15 cm/min, 5 cm/min and 15 cm/min, 10 cm/min and 15 cm/min, or 5 cm/min and 10 cm/min). In some embodiments, the isoprenoid composition is exposed to the resin with a maximum downflow superficial velocity of between 5 cm/min and 11 cm/min (e.g., 5 cm/min, 6 cm/min, 7 cm/min, 8 cm/min, 9 cm/min, 10 cm/min, or 11 cm/min). In some embodiments, the isoprenoid composition is exposed to the resin with a maximum upflow superficial velocity of between 0.1 cm/min and 10 cm/min (e.g., between 0.1 cm/min and 8 cm/min, 0.1 cm/min and 6 cm/min, 0.1 cm/min and 4 cm/min, 0.1 cm/min and 1 cm/min, 1 cm/min and 10 cm/min, 3 cm/min and 10 cm/min, 5 cm/min and 10 cm/min, 8 cm/min and 10 cm/min, 4 cm/min and 8 cm/min, or 2 cm/min and 6 cm/min). In some embodiments, the isoprenoid composition is exposed to the resin with a maximum upflow superficial velocity of between 1 cm/min and 5 cm/min (e.g., 1 cm/min, 2 cm/min, 3 cm/min, 4 cm/min, or 5 cm/min). In some embodiments, the steps (a) through (c) are repeated from 2 to 20 times (e.g., 2, 3, 4, 5, 6, 7, 8, 9, 10, 11, 12, 13, 14, 15, 16, 17, 18, 19, or 20 times). In some embodiments, the steps (a) through (c) are repeated from 2 to 10 times (e.g., 2, 3, 4, 5, 6, 7, 8, 9, or 10 times). In some embodiments, the steps (a) through (c) are repeated 6 times. In some embodiments, the steps (a) through (c) are repeated from 2 to 4 times (e.g., 2, 3, or 4 times).

In some embodiments, the resin is regenerated following the collection of the isoprenoid from the resin in step (c). In some embodiments, the resin is regenerated by: (a) adding a polar solvent to the resin; (b) removing the methanol from the resin; (c) heating the resin; and (d) cooling the resin. In some embodiments, step (a) is performed by adding a polar solvent to the resin in an amount of between 1 BV and 10 BV (e.g., 1 BV, 2 BV, 3 BV, 4 BV, 5 BV, 6 BV, 7 BV, 8 BV, 9 BV, or 10 BV). In some embodiments, the polar solvent is added to the resin in an amount of between 2 BV and 6 BV (e.g., 1 BV, 2 BV, 3 BV, 4 BV, 5 BV, or 6 BV). In some embodiments, the polar solvent is added to the resin in an amount of about 4 BV. In some embodiments, step (c) is performed by heating the resin to a temperature of between 100° C. and 200° C. (e.g., between 100° C. and 180° C., 100° C. and 160° C., 100° C. and 140° C., 100° C. and 120° C., 120° C. and 200° C., 150° C. and 200° C., 170° C. and 200° C., 140° C. and 180° C., or 120° C. and 160° C.). In some embodiments, the resin is heated to a temperature of about 150° C. In some embodiments, the polar solvent is methanol. In some embodiments, the polar solvent is isopropanol. In some embodiments, the cooling of step (d) is performed by cooling the resin to room temperature. In some embodiments, the chromatography is performed under $N_2$.

In some embodiments, the isoprenoid is a $C_5$-$C_{60}$ isoprenoid (e.g., $C_5$-$C_{50}$ isoprenoid, $C_5$-$C_{40}$ isoprenoid, $C_5$-$C_{30}$ isoprenoid, $C_5$-$C_{20}$ isoprenoid, $C_5$-$C_{10}$ isoprenoid, $C_{10}$-$C_{60}$ isoprenoid, $C_{20}$-$C_{60}$ isoprenoid, $C_{30}$-$C_{60}$ isoprenoid, $C_{40}$-$C_{60}$ isoprenoid, $C_{50}$-$C_{60}$ isoprenoid, $C_{10}$-$C_{40}$ isoprenoid, $C_{20}$-$C_{50}$ isoprenoid, $C_{20}$-$C_{30}$ isoprenoid, $C_{15}$-$C_{30}$ isoprenoid, or $C_{30}$-$C_{50}$ isoprenoid). In some embodiments, the isoprenoid is a $C_{15}$-$C_{60}$ isoprenoid (e.g., $C_{15}$-$C_{50}$ isoprenoid, $C_{15}$-$C_{40}$ isoprenoid, $C_{15}$-$C_{30}$ isoprenoid, $C_{15}$-$C_{20}$ isoprenoid, $C_{20}$-$C_{60}$ isoprenoid, $C_{30}$-$C_{60}$ isoprenoid, $C_{40}$-$C_{60}$ isoprenoid, $C_{50}$-$C_{60}$ isoprenoid, $C_{25}$-$C_{40}$ isoprenoid, $C_{30}$-$C_{50}$ isoprenoid, $C_{20}$-$C_{40}$ isoprenoid, $C_{20}$-$C_{50}$ isoprenoid, $C_{20}$-$C_{30}$ isoprenoid, $C_{15}$-$C_{30}$ isoprenoid, or $C_{30}$-$C_{50}$ isoprenoid). In some embodiments, the isoprenoid is a hemiterpenoid, monoterpenoid, sesquiterpenoid, diterpenoid, sesterterpenoid, triterpenoid, tetraterpenoid, or polyterpenoid. In some embodiments, the isoprenoid is a sesquiterpenoid. In some embodiments, the isoprenoid is a hemiterpene, monoterpene, sesquiterpene, diterpene, sesterterpene, triterpene, tetraterpene, or polyterpene. In some embodiments, the isoprenoid is a sesquiterpene. In some embodiments, the isoprenoid is a monoterpenoid. In some embodiments, the isoprenoid is abietadiene, amorphadiene, cadinane, carene, cuminaldehyde, eugenol, farnesene, geranial, isoprene, limonene, myrcene, ocimene, α-pinene, β-pinene, sabinene, γ-terpinene, terpinolene, thujone, neral, eucalyptol, citronellal, carvone, or valencene. In some embodiments, the isoprenoid is purified from the isoprenoid composition with a purity of from about 95% (w/w) to about 100% (w/w) (e.g., 95% (w/w) to 100% (w/w) or more, e.g., 95% (w/w), 95.5% (w/w), 96% (w/w), 96.5% (w/w), 97% (w/w), 97.5% (w/w), 98% (w/w), 98.5% (w/w), 99% (w/w), 99.5% (w/w) or 100% (w/w), or more). In some embodiments, the isoprenoid is purified from the isoprenoid composition with a purity of from about 98% (w/w) to about 100% (w/w) (e.g., 98% (w/w), 98.1% (w/w), 98.2 wt, 98.3% (w/w), 98.4% (w/w), 98.5% (w/w), 98.6% (w/w), 98.7% (w/w), 98.8% (w/w), 98.9% (w/w), 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). In some embodiments, the isoprenoid is purified from the isoprenoid composition with a purity of from about 99% (w/w) to about 100% (w/w) (e.g., 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). In some embodiments, the is purified from the isoprenoid composition with a purity of from about 99.5% (w/w) to about 100% (w/w) (e.g., 99.5% (w/w), 99.6% (w/w), 99.7% (w/w), 99.8% (w/w), 99.9% (w/w), or 100% (w/w)).

In an aspect, the disclosure provides a composition comprising an isoprenoid, wherein the composition is produced by anyone of the methods described herein. In some embodiments, the isoprenoid has a purity of from about 95% (w/w) to about 100% (w/w) (e.g., 95% (w/w) to 100% (w/w) or more, e.g., 95% (w/w), 95.5% (w/w), 96% (w/w), 96.5% (w/w), 97% (w/w), 97.5% (w/w), 98% (w/w), 98.5% (w/w), 99% (w/w), 99.5% (w/w) or 100% (w/w), or more).

In some embodiments, the isoprenoid has a purity of from about 98% (w/w) to about 100% (w/w) (e.g., 98% (w/w), 98.1% (w/w), 98.2 wt, 98.3% (w/w), 98.4% (w/w), 98.5% (w/w), 98.6% (w/w), 98.7% (w/w), 98.8% (w/w), 98.9% (w/w), 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)), optionally wherein the isoprenoid is purified from the isoprenoid composition with a purity of from about 99% (w/w) to about 100% (w/w) (e.g., 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). In some embodiments, the isoprenoid has a purity of from about 99.5% (w/w) to about 100% (w/w) (e.g., 99.5% (w/w), 99.6% (w/w), 99.7% (w/w), 99.8% (w/w), 99.9% (w/w), or 100% (w/w)). In some embodiments, the composition comprises one or more impurities comprising farnesoic acid, farnesol, farnesene oxide, farnesene epoxide, a fatty acid, a sterol, HHFA, santalene, or santalol.

In an aspect, the disclosure provides a composition comprising an isoprenoid and one or more impurities, wherein the purity of the isoprenoid is from about 90% (w/w) to about 100% (w/w), and wherein the one or more impurities comprise farnesoic acid, farnesol, farnesene oxide, farnesene epoxide, a fatty acid, a sterol, HHFA, santalene, or santalol. In some embodiments, the composition comprises farnesol having a concentration of farnesol is between 0 mg/ml and 1 g/L (e.g., between 0.2 g/L and 1 g/L, 0.4 g/L and 1 g/L, 0.6 g/L, 0.6 g/L and 1 g/L, 0.8 g/L and 1 g/L, 0 mg/mL, and 0.8 g/L, 0 mg/mL and 0.6 g/L, 0 mg/ml and 0.4 g/L, 0 mg/mL and 0.2 g/L, 0.4 g/L and 0.6 g/L, or 0.2 g/L and 0.8 g/L). In some embodiments, the concentration of farnesol is between 0 mg/L and 600 mg/L (e.g., between 0 mg/mL and 500 mg/mL, 0 mg/mL and 400 mg/mL, 0 mg/mL and 300 mg/mL, 0 mg/mL and 200 mg/mL, 0 mg/ml and 100 mg/mL, 100 mg/mL and 600 mg/mL, 200 mg/ml and 600 mg/mL, 300 mg/ml and 600 mg/mL, 400 mg/mL and 600 mg/mL, 500 mg/mL and 600 mg/mL, 200 mg/ml and 400 mg/mL, or 300 mg/mL and 500 mg/mL). In some embodiments, the concentration of farnesol is less than 500 mg/L.

In some embodiments, the composition comprises farnesene epoxide having a concentration of farnesol is between 0 mg/ml and 500 mg/L (e.g., between 0 mg/mL and 400 mg/mL, 0 mg/ml and 300 mg/mL, 0 mg/mL and 200 mg/mL, 0 mg/mL and 100 mg/mL, 100 mg/mL and 500 mg/mL, 200 mg/mL and 500 mg/mL, 300 mg/ml and 500 mg/mL, 400 mg/mL and 500 mg/mL, 200 mg/mL and 400 mg/mL, or 100 mg/mL and 300 mg/mL). In some embodiments, the concentration of farnesene epoxide is between 0 mg/L and 200 mg/L (e.g., between 0 mg/L and 150 mg/L, 0 mg/L and 100 mg/L, 0 mg/L and 50 mg/L, 50 mg/L and 200 mg/L, 100 mg/L and 200 mg/L, 150 mg/L and 200 mg/L, 20 mg/L and 100 mg/L, or 50 mg/L and 150 mg/L). In some embodiments, the concentration of farnesene epoxide is less than 150 mg/L.

In an aspect, the disclosure provides a composition comprising an isoprenoid and one or more carriers, diluents, or excipients, wherein the purity of the isoprenoid is from about 99.5% (w/w) to about 100% (w/w) (e.g., 99.5% (w/w), 99.6% (w/w), 99.7% (w/w), 99.8% (w/w), 99.9% (w/w), or 100% (w/w)). In some embodiments, the isoprenoid is present with one or more impurities, and wherein the one or more impurities is present in a concentration of about 0.5% (w/w) or less.

In some embodiments, the one or more impurities is present in a concentration of about 0.4% (w/w) or less. In some embodiments, the one or more impurities is present in a concentration of about 0.3% (w/w) or less. In some embodiments, the one or more impurities is present in a concentration of about 0.2% (w/w) or less. In some embodiments, the one or more impurities is present in a concentration of about 0.1% (w/w) or less. In some embodiments, the one or more impurities comprise farnesoic acid, farnesol, farnesene oxide, farnesene epoxide, a fatty acid, a sterol, HHFA, santalene, or santalol.

Definitions

As used in this specification and the appended claims, the singular forms "a," "an," and "the" include plural reference unless the context clearly dictates otherwise.

The term "about" when modifying a numerical value or range herein includes normal variation encountered in the field, and includes plus or minus 1-10% (e.g., 1%, 2%, 3%, 4%, 5%, 6%, 7%, 8%, 9% or 10%) of the numerical value or end points of the numerical range. Thus, a value of 10 includes all numerical values from 9 to 11. All numerical ranges described herein include the endpoints of the range unless otherwise noted, and all numerical values in-between the end points, to the first significant digit.

As used herein "acidic aluminum oxide" refers to an amphoteric oxide comprising the chemical formula of $Al_2O_3$ having a pH, when exposed to an aqueous environment (e.g., when contacted with water), of about ≤4.5.

As used herein "basic aluminum oxide" refers to an amphoteric oxide comprising the chemical formula of $Al_2O_3$ having a pH, when exposed to an aqueous environment (e.g., when contacted with water), of about ≥10.

As used herein, the term "bulk density" refers to the weight of a volume unit of powder and is usually expressed in $g/cm^3$, $kg/m^3$, g/100 mL, or g/mL. Bulk density is usually determined by measuring the volume of 100 g of powder in a 250 ml graduated cylinder after exposure to compaction by standardized tapping.

As used herein, the term "capable of producing" refers to a host cell which includes the enzymes necessary for the production of a given compound in accordance with a biochemical pathway that produces the compound. For example, a cell (e.g., a yeast cell) that is "capable of producing" an isoprenoid is one that contains the enzymes necessary for production of the isoprenoid according to the isoprenoid biosynthetic pathway.

As used herein, the term "evaporation" describes a process by which at least a portion of a liquid undergoes a state change to have a gaseous state. For example, evaporation may be used to separate two liquids from one another or to remove one liquid from a mixture containing one or more additional liquids. In some embodiments, evaporation includes the process of distillation, in which a liquid not only changes phase to a gaseous state but is subsequently condensed back to a liquid form. In some embodiments of the disclosure, a distillation is performed by heating a mixture of liquids such that a lower-boiling point substance begins to evaporate, changing phase from a liquid to a gaseous state, while leaving the remaining liquid(s) in the mixture in a liquid phase. The lower-boiling point substance may then be condensed, e.g., upon exposure to reduced temperature, thereby: (1) returning the lower-boiling point substance to a liquid phase, and (2) separating the lower-boiling point substance from the remaining liquid(s) in the mixture.

The distillation may be, for example, a "simple distillation," which refers to a process in which a mixture of liquids having substantially different boiling points (e.g., boiling points that differ from one another by about 25 C.° or more) is separated by heating the mixture until substantially all of the lower-boiling point substance evaporates and substantially all of the higher-boiling point substance remains in the liquid phase. The vapor of the lower-boiling point substance, in turn, is condensed so as to return the lower-boiling point substance to the liquid phase. In some embodiments, the distillation may be a "fractional distillation," a process that is used, e.g., for separating highly miscible liquids and/or those having boiling points that differ by less than about 25 C°. A fractional distillation process involves heating a mixture containing the liquids such that the resulting vapor enters a fractionating column. The fractionating column is a column (e.g., a vertical, inclined, or horizontal column) configured so as to have a temperature gradient: the bottom of the fractionating column (i.e., the point at which the vapor enters the column) is the warmest, and the top of the fractionating column is the coolest. As the vapor proceeds upward through the column, the vapor is enriched for the lower-boiling point substance as a result of the temperature gradient. Once enriched for the lower-boiling point substance, the vapor exits the fractionating column and is exposed to a reduced temperature, thereby condensing the lower-boiling point substance and resolving the liquid mixture into its components.

As used herein, the term "pharmaceutical composition" refers to a mixture containing a therapeutic compound or prophylactic compound to be administered to a subject, such as a mammal, e.g., a human, in order to prevent, treat or control a particular disease or condition affecting or that may affect the mammal.

As used herein, the term "farnesene composition" refers to a mixture (e.g., a solution or suspension) comprising farnesene. In some embodiments, the farnesene composition comprises farnesene and one or more impurities.

As used herein "neutral aluminum oxide" refers to an amphoteric oxide comprising the chemical formula of $Al_2O_3$ and having a pH, when exposed to an aqueous environment (e.g., when contacted with water), of about 7.

As used herein, the term "pharmaceutically acceptable" refers to those compounds, materials, compositions and/or dosage forms which are suitable for contact with the tissues of a subject, such as a mammal (e.g., a human) without excessive toxicity, irritation, allergic response, or other deleterious complications commensurate with a reasonable benefit/risk ratio.

As used herein, the term "pharmaceutically acceptable salt" means any pharmaceutically acceptable salt of a compound described herein. For example, pharmaceutically acceptable salts of any of the compounds described herein include those that are within the scope of sound medical judgment, suitable for use in contact with the tissues of humans and animals without undue toxicity, irritation, or allergic response, and are commensurate with a reasonable benefit/risk ratio. Examples of pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. Such salts can be prepared, for example, in situ during the final isolation and purification of a compound described herein or separately by reacting a free base group with a suitable organic acid.

The compounds described herein may have ionizable groups so as to be capable of preparation as pharmaceutically acceptable salts. These salts may be acid addition salts involving inorganic or organic acids or the salts may, in the case of acidic forms of the compounds described herein, be prepared from inorganic or organic bases. The compounds may be prepared or used as pharmaceutically acceptable salts synthesized as addition products of pharmaceutically acceptable acids or bases. Suitable pharmaceutically acceptable salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

As used herein, the term "polar solvent" refers to a solution which possesses charge separation, and the ability to solvate other polar materials. For example, the polar solvents include, but are not limited to acetone, acetonitrile, ethyl acetate, dimethylformamide (DMF), dimethylsulfoxide (DMSO), isopropanol, and methanol.

As used herein, the terms "pore volume" or "porosity" refer to a measure of the void spaces in a material. These parameters are commonly measured as a volume percentage. The volume percentage may be expressed as the volume of voids in a material over the total volume of the material. The pore volume is usually expressed in terms of mL/g, $cm^3/g$, or $m^3/kg$.

As used herein, the term "production" generally refers to an amount of compound produced by a host cell provided herein. In some embodiments, production is expressed as a yield of the compound by the host cell. In other embodiments, production is expressed as a productivity of the host cell in producing the compound.

As used herein, the term "residence time" refers to the total amount of time a material (e.g., a solvent or isoprenoid composition described herein, such as a farnesene composition) remains on the column during a column chromatography procedure. A material (e.g., a solvent or isoprenoid composition described herein, such as a farnesene composition) having a faster flow rate will have a shorter residence time in comparison to a material (e.g., a solvent or isoprenoid composition described herein, such as a farnesene composition) having a slower flow rate. Likewise, a material (e.g., a solvent or isoprenoid composition described herein, such as a farnesene composition) having a slower flow rate will have a longer residence time in comparison to a material (e.g., a solvent or isoprenoid composition described herein, such as a farnesene composition) having a faster flow rate.

As used herein, the term "silica" refers to silicon dioxide ($SiO_2$) based resin materials which may be used, e.g., in a column chromatography procedure. The term "silica" embraces, inter alia, amorphous forms of silica that consist of irregular 3-dimensional structures, which are porous materials with microscale to nanoscale pores.

As used herein, the terms "subject" and "patient" are interchangeable and refer to an organism that receives therapeutic or prophylactic treatment for a particular disease or condition as described herein. Examples of subjects and patients include mammals, such as humans.

As used herein in the context of a column chromatography procedure, the term "superficial velocity" refers to the volumetric flow rate of a fluid divided by the cross-sectional area of the empty column over which the fluid is being passed. Thus, the superficial velocity is not influenced in any way by the existence or structure of the packed bed and does not change depending upon whether the particles in the bed are porous or nonporous.

As used herein, the term "water content" refers to the amount of water bound to a resin which is characterized in terms of the percentage of the resin weight which comes from the water bound to the resin. The amount of moisture absorbed by resins may depend on various factors, including resin type, ambient temperature, seasonal changes, packaging and transportation issues, and manufacturing.

As used herein, the term "wetting" refers to contacting a resin with a solvent containing a dissolved material for isolation. For example, in some embodiments, "wetting" occurs when a mixture comprising an isoprenoid compound contacts the resin.

BRIEF DESCRIPTION OF THE DRAWINGS

FIG. 1 shows the components of the resulting high purity farnesene product.

FIG. 3 is a graph showing the breakthrough data of santalols after alumina column treatment, which reduced santalols from over 12000 ppm to below detection level for the first three bed volumes (BV).

FIG. 5 is a graph showing the concentration of products over time upon treatment of farnesene with $H_3PO_4$.

DETAILED DESCRIPTION

Figure 2A:
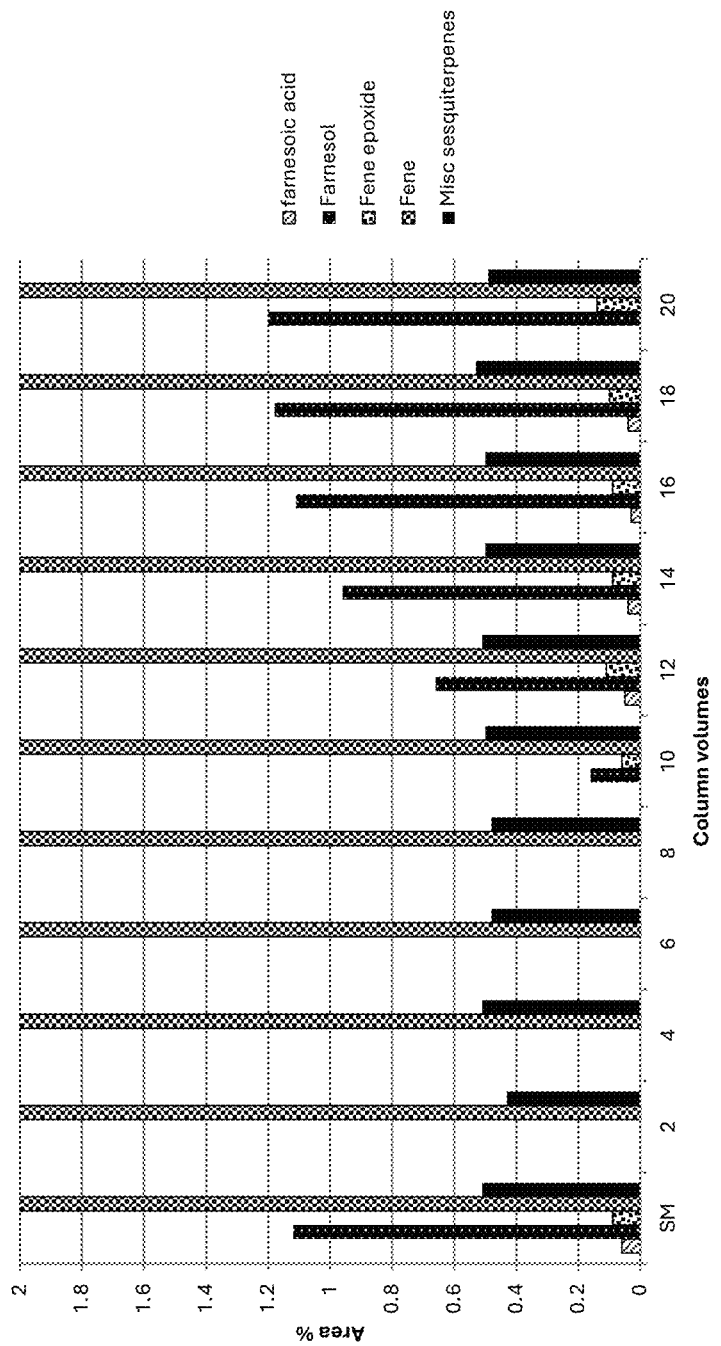
FIG. 2A-FIG. 2C are a set of graphs showing resulting purity of farnesene isolated by the removal of farnesene epoxide, farnesol, and farnesoic acid by alumina stripping performed using basic alumina from Sorbent Technology (FIG. 2A), basic alumina from Sigma Aldrich (FIG. 2B), and Activity Super I activated alumina from Sorbent Technology (FIG. 2C).

The present disclosure provides methods of isolating an isoprenoid such that the resulting isoprenoid is highly pure. The isoprenoid may be isolated from any source such as a fermentation composition, a plant, or animal. Given the interest in producing and isolating isoprenoids with a high-purity, the challenge of purifying isoprenoids with high purity has been significant. For example, isoprenoids that are purified using traditional distillation techniques result in an isoprenoid composition with insufficient purity for certain applications such as polymerization reactions.

It has presently been discovered that combining a unique series of chromatography steps results in isoprenoid compositions having remarkable levels of purity (e.g., levels of purity of 99.5% (w/w) and above). For example, using the methods and compositions described herein, an isoprenoid may be purified from a composition comprising the isoprenoid. To recover the isoprenoid with high purity from the isoprenoid composition, the composition may be subject to one or more chromatography step, where the isoprenoid composition contacts a resin at a specified flow rate, wherein the resin has been prepared and is regenerated after contacting the isoprenoid solution. Repetition of these steps results in a high purity isoprenoid product suitable for use in polymerization reactions, for example. The present disclosure is based on, at least in part, Applicant's discovery that the chromatography steps described herein were capable of removing even very high levels of impurities (e.g., >10,000 ppm) from the isoprenoid efficiently. This is in contrast to other tested methods, which resulted in higher levels of impurities.

The sections that follow provide a description of exemplary compositions and methods that may be used to perform the chromatography steps of the disclosure.

Isoprenoids

Described herein are methods of purifying an isoprenoid, methods of isolating an isoprenoid from an isoprenoid source, as well as methods of making an isoprenoid having high purity. The isoprenoid of the disclosure may be a $C_5$-$C_{60}$ isoprenoid (e.g., a $C_5$ isoprenoid, $C_{10}$ isoprenoid, $C_{15}$ isoprenoid, $C_{20}$ isoprenoid, $C_{25}$ isoprenoid, $C_{30}$ isoprenoid, $C_{35}$ isoprenoid, $C_{40}$ isoprenoid, $C_{45}$ isoprenoid, $C_{50}$ isoprenoid, $C_{55}$ isoprenoid, or $C_{60}$ isoprenoid). For example, in some embodiments, the isoprenoid is a $C_{20}$ isoprenoid. In some embodiments, the isoprenoid is a $C_{60}$ isoprenoid. These compounds are derived from four isoprene units and also called diterpenoids. Illustrative examples of diterpenoids are casbene, eleutherobin, paclitaxel, prostratin, pseudopterosin, taxadiene, and salvinorins. In yet other examples, the isoprenoid is a $C_{20+}$ isoprenoid. These compounds are derived from more than four isoprene units and include: triterpenoids ($C_{30}$ isoprenoid compounds derived from 6 isoprene units) such as arbrusidee, bruceantin, testosterone, progesterone, cortisone, digitoxin, and squalene; tetraterpenoids ($C_{40}$ isoprenoid compounds derived from 8 isoprenoids) such as β-carotene; and polyterpenoids ($C_{40+}$ isoprenoid compounds derived from more than 8 isoprene units) such as polyisoprene. In some embodiments, the isoprenoid is selected from the group consisting of abietadiene, amorphadiene, cadinane, carene, cuminaldehyde, eugenol, farnesene, geranial, isoprene, limonene, myrcene, ocimene, α-pinene, β-pinene, sabinene, γ-terpinene, terpinolene, thujone, neral, eucalyptol, citronellal, carvone, and valencene. In some embodiments, the isoprenoid is cadinene. In some embodiments, the isoprenoid is farnesene.

The isoprenoid product may be a $C_5$-$C_{20}$ isoprenoid (e.g., $C_5$ isoprenoid, $C_6$ isoprenoid, $C_7$ isoprenoid, $C_8$ isoprenoid, $C_9$ isoprenoid, $C_{10}$ isoprenoid, $C_{11}$ isoprenoid, $C_{12}$ isoprenoid, $C_{13}$ isoprenoid, $C_{14}$ isoprenoid, $C_{15}$ isoprenoid, $C_{16}$ isoprenoid, $C_{17}$ isoprenoid, $C_{18}$ isoprenoid, $C_{19}$ isoprenoid, or $C_{20}$ isoprenoid). In some embodiments, the isoprenoid produced by the cell is a $C_5$ isoprenoid. These compounds are derived from one isoprene unit and are also called hemiterpenoids. Illustrative examples of a hemiterpenoid are isoprene and isoprenol.

The isoprenoid product may be a $C_{10}$-$C_{15}$ isoprenoid (e.g., $C_{10}$ isoprenoid, $C_{11}$ isoprenoid, $C_{12}$ isoprenoid, $C_{13}$ isoprenoid, $C_{14}$ isoprenoid, or $C_{15}$ isoprenoid). In other embodiments, the isoprenoid is a $C_{10}$ isoprenoid. These compounds are derived from two isoprene units and are also called monoterpenoids. Illustrative examples of monoterpenoids are limonene, citronellol, geraniol, menthol, perillyl alcohol, linalool, thujone, myrcene, hinokitiol, carvacrol, anethole, cuminaldehyde, eucalyptol, α-pinene, β-pinene, citronellal, isopulegol, nerol, neral, geranial, and carvone. In other embodiments, the isoprenoid is a $C_{15}$ isoprenoid. These compounds are derived from three isoprene units and are also called sesquiterpenoids. Illustrative examples of sesquiterpenoids are periplanone B, gingkolide B, amorphadiene, artemisinin, artemisinic acid, valencene, nootkatone, epicedrol, epiaristolochene, farnesol, gossypol, sanonin, periplanone, forskolin, and patchoulol, which is also known as patchouli alcohol.

Isoprenoid compounds also include, but are not limited to, carotenoids (such as lycopene, α- and β-carotene, α- and β-cryptoxanthin, bixin, zeaxanthin, astaxanthin, and lutein), steroid compounds, cannabinoids, and compounds that are composed of isoprenoids modified by other chemical groups, such as mixed terpene-alkaloids, and coenzyme Q (CoQ) enzymes, such as, for example, coenzyme Q-10.

In some embodiments, the isoprenoid is a hemiterpenoid, monoterpenoid, sesquiterpenoid, diterpenoid, sesterterpenoid, triterpenoid, tetraterpenoid, or polyterpenoid. In some embodiments, the isoprenoid is a monoterpenoid.

Terpenes

In some embodiments, the product that is isolated is a terpene. In some embodiments, the terpene is a $C_5$-$C_{60}$ terpene (e.g., a $C_5$ isoprenoid, $C_{10}$ isoprenoid, $C_{15}$ isoprenoid, $C_{20}$ isoprenoid, $C_{25}$ isoprenoid, $C_{30}$ isoprenoid, $C_{35}$ isoprenoid, $C_{40}$ isoprenoid, $C_{45}$ isoprenoid, $C_{50}$ isoprenoid, $C_{55}$ isoprenoid, or $C_{60}$ isoprenoid). In some embodiments, the terpene is a $C_5$-$C_{20}$ terpene (e.g., $C_5$ terpene, $C_6$ terpene, $C_7$ terpene, $C_8$ terpene, Co terpene, $C_{10}$ terpene, $C_{11}$ terpene, $C_{12}$ terpene, $C_{13}$ terpene, $C_{14}$ terpene, $C_{15}$ terpene, $C_{16}$ terpene, $C_{17}$ terpene, $C_{18}$ terpene, $C_{19}$ terpene, or $C_{20}$ terpene). In some embodiments, the terpene is a $C_{10}$-$C_{15}$ terpene (e.g., $C_{10}$ terpene, $C_{11}$ terpene, $C_{12}$ terpene, $C_{13}$ terpene, $C_{14}$ terpene, or $C_{15}$ terpene). In some embodiments, the terpene is a hemiterpene, monoterpene, sesquiterpene, diterpene, sesterterpene, triterpene, tetraterpene, or polyterpene. In some embodiments, terpene is a sesquiterpene.

In some embodiments, the terpene is a monoterpene. Monoterpenes are $C_{10}$ terpenes and are derived from two isoprene units. For example, the monoterpene may be carene, whose structure is:

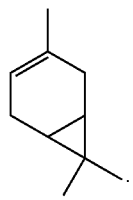

Carene is typically made from GPP by carene synthase. Illustrative examples of suitable nucleotide sequences include but are not limited to: (AF461460, REGION 43 . . . 1926; *Picea abies*) and (AF527416, REGION: 78 . . . 1871; *Salvia stenophylla*) for use as heterologous sequences that encode carene synthase. Another monoterpene, such as geraniol, (also known as rhodnol), whose structure is

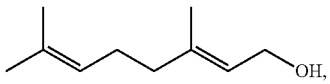

may be a product produced by the present invention. Geraniol is typically made from OPP by geraniol synthase. Illustrative examples of suitable nucleotide sequences include but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*) for encoding geraniol synthase that may be used a heterologous sequence of the present invention. The monoterpene, linalool, whose structure is:

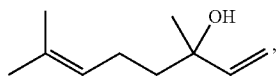

is typically made from GPP by linalool synthase and may be produced by the present invention. Illustrative examples of a suitable nucleotide sequence include, but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM-463918, Locus XP-463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. *crispa* cultivar No. 79). These sequences may be used as heterologous sequences of the present invention. Another monoterpene, limonene whose structure is:

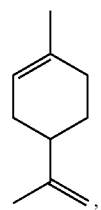

is typically made from GPP by limonene synthase. Illustrative examples of suitable nucleotide sequences that may be used as heterologous sequences of the present invention include but are not limited to: (+)-limonene synthases (AF514287, REGION: 47 . . . 1867; *Citrus limon*) and (AY055214, REGION: 48 . . . 1889; *Agastache rugosa*) and (−)-limonene synthases (DQ195275, REGION: 1 . . . 1905; *Picea sitchensis*), (AF006193, REGION: 73.1986; *Abies grandis*), and (MC4SLSP, REGION: 29 . . . 1828; *Mentha spicata*).

The monoterpene, myrcene, whose structure is:

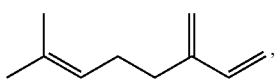

is typically made from GPP by myrcene synthase and is another product that may be produced by the present invention. Illustrative examples of suitable nucleotide sequences that may be used as heterologous sequences of the present invention include but are not limited to: (187908; *Abies grandis*), (AY195609; *Antirrhinum majus*), (AY195608; *Antirrhinum majus*), (NM_127982; *Arabidopsis thaliana* TPS10), NM_113485; *Arabidopsis thaliana* ATTPS-CIN), (NM_13483; *Arabidopsis thaliana* ATIPS-CIN), (AF271259; *Perilla frutescens*), (AY473626; *Picea abies*), (AF369919; *Picea abies*), and (AJ304839; *Quercus ilex*).

Another monoterpene, ocimene, α- and β-Ocimene, whose structures are:

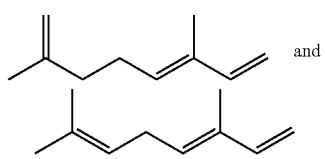

respectively, are typically made from GPP by ocimene synthase, a synthase that may be encoded by the heterologous sequences of the present invention. Illustrative examples of suitable nucleotide sequences that may be used as heterologous sequences include but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

Another monoterpene, α-pinene whose structure is:

is typically made from GPP by α-pinene synthase, a synthase that may be encoded by the heterologous sequences of the present invention. Illustrative examples of suitable nucleotide sequences that may be used as heterologous sequences to encode the synthase include but are not limited to: (+) α-pinene synthase (AF543530, REGION: 1 . . . 1887; *Pinus taeda*), (−) α-pinene synthase (AF543527, REGION: 32 . . . 1921; *Pinus taeda*), and (+)/(−) α-pinene synthase (AGU87909, REGION: 6111892; *Abies grandis*).

Another monoterpene, β-pinene, whose structure is:

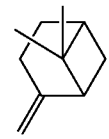

is typically made from GPP by β-pinene synthase, a synthase that may be encoded by the heterologous sequences of the present invention. Illustrative examples of suitable nucleotide sequences that may be used as heterologous sequences to encode the synthase include but are not limited to: (−) β-pinene synthases (AF276072, REGION: 1 . . . 1749; *Artemisia annua*) and (AF514288, REGION: 26 . . . 1834; *Citrus limon*).

Another monoterpene, sabinene, whose structure is:

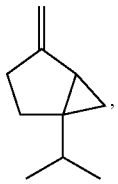

is typically made from GPP by sabinene synthase, a synthase that may be encoded by the heterologous sequences of the present invention. An illustrative example of a suitable nucleotide sequence that may be used as a heterologous sequence of include but is not limited to AF051901, REGION: 26 . . . 1798 from *Salvia officinalis*.

Another monoterpene, γ-terpinene, whose structure is:

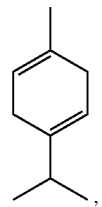

is typically made from GPP by a γ-terpinene synthase, a synthase that may be encoded by the heterologous sequences of the present invention. Illustrative examples of suitable nucleotide sequences that may be used as heterologous sequences include but are not limited to: (AF514286, REGION: 30 . . . 1832 from *Citrus limon*) and (AB110640, REGION 1 . . . 1803 from *Citrus unshiu*).

Another monoterpene, terpinolene, whose structure is

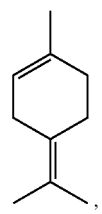

is typically made from GPP by terpinolene synthase, a synthase that may be encoded by the heterologous sequences of the present invention. Illustrative examples of suitable nucleotide sequences that may be used as heterologous sequences include but are not limited to: (AY693650 from *Ocimum basilicum*) and (AY906866, REGION: 10 . . . 1887 from *Pseudotsuga menziesii*).

In some embodiments, the product is abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, menthol, eucalyptol, citronellol, citronellal, or valencene. In some embodiments, the isolated product is cadinane, wherein cadinane has the structure of:

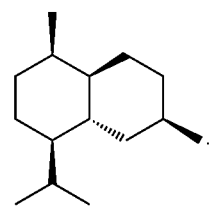

In some embodiments, the isolated product is farnesene. In some embodiments, the product is β-farnesene having the structure of:

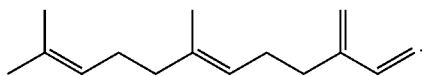

In some embodiments, the product is myrcene. In some embodiments, the product is pinene. In some embodiments, the product is limonene.

Methods of Isolating an Isoprenoid

Described herein are methods of purifying an isoprenoid, methods of isolating an isoprenoid from an isoprenoid source, as well as methods of making an isoprenoid having high purity. The methods described herein may include, for example, in some cases isolating farnesene from an evaporated (e.g., distilled) farnesene composition to recover farnesene product in high purity. Exemplary potential chromatography steps are described in further detail in the section that follows.

The isoprenoid may in some cases be isolated from an evaporated isoprenoid composition (e.g., distilled isoprenoid). For example, the isoprenoid may be isolated from an evaporated isoprenoid composition which resulted from distillation of a composition comprising the isoprenoid, wherein the composition resulted from an extraction. The distillation may be performed using any procedure known in the art. In some embodiments, the distillation may be a simple distillation. In some embodiments, the distillation may be a fractional distillation.

The resulting isoprenoid composition may include one or more impurities. The isoprenoid composition may include the isoprenoid and one or more impurities. One or more of the impurities may be a polar impurity. For example, a polar impurity may include farnesoic acid, farnesol, farnesene oxide, farnesene epoxide, a fatty acid, a sterol, hexahydrofarnesoic acid (HHFA), santalene, or santalol. The one or more impurities may be present in an amount of between 1 ppm and 15,000 ppm (e.g., between 1 ppm and 10,000 ppm, 1 ppm and 5,000 ppm, 1 ppm and 1,0000 ppm, 1 ppm and 500 ppm, 1 ppm and 100 ppm, 100 ppm and 15,000 ppm, 1,000 ppm and 15,000 ppm, 5,000 ppm and 15,000 ppm, 10,000 ppm and 15,000 ppm, 5,000 ppm and 12,000 ppm, 1,000 ppm and 10,000 ppm, or 3,000 ppm and 14,000 ppm). For example, the isoprenoid composition has a concentration of one or more impurities of between 1000 ppm and 12,000 ppm (e.g., between 1000 ppm and 10,000 ppm, 1000 ppm and 8,000 ppm, 1000 ppm and 5,000 ppm, 1000 ppm and 2,000 ppm, 2,000 ppm and 12,000 ppm, 5,000 ppm and 12,000 ppm, 8,000 ppm and 12,000 ppm, 10,000 ppm and 12,000 ppm, 5,000 ppm to 10,000 ppm, or 3,000 ppm to 10,000 ppm). In some embodiments the isoprenoid composition has a concentration of one or more impurities of between 100 ppm and 1,000 ppm (e.g., between 100 ppm and 800 ppm, 100 ppm and 600 ppm, 100 ppm and 400 ppm, 100 ppm and 200 ppm, 200 ppm and 1,000 ppm, 500 ppm and 1,000 ppm, 800 ppm and 1,000 ppm, or 300 ppm to 800 ppm). In some embodiments, an antioxidant may be added to the composition. For example, the antioxidant may be 4-tert butylcatechol. In some embodiments, the 4-tert butylcatechol is added to the farnesene composition to a concentration of from 50 ppm to 150 ppm (e.g., from 50 ppm to 125 ppm, 50 ppm to 100 ppm, 50 ppm to 75 ppm, 75 ppm to 150 ppm, 100 ppm to 150 ppm, 125 to 150 ppm, or 25 ppm to 75 ppm). In some embodiments, the 4-tert butylcatechol is added to the farnesene composition to a concentration of about 100 ppm.

Chromatography

Disclosed herein are methods of purifying an isoprenoid comprising providing an isoprenoid composition and purifying the isoprenoid from the isoprenoid composition by way of chromatography. For example, described herein are methods of purifying farnesene comprising providing a farnesene composition and purifying the farnesene from the farnesene composition by way of chromatography.

In some embodiments, chromatography is used to isolate an isoprenoid, such as following extraction and evaporation of the isoprenoid from an isoprenoid source of the disclosure. In some embodiments, chromatography is used to isolate the isoprenoid from an isoprenoid composition. The chromatography may include pre-wetting a resin; exposing the isoprenoid composition to the resin; and collecting the isoprenoid from the resin. The chromatography step may include, for example, exposing the isoprenoid composition to a resin and recovering the isoprenoid from the resin.

The resin may be aluminum oxide resin, such as basic aluminum oxide resin, an acidic aluminum oxide resin, or a neutral aluminum oxide resin. In some embodiments, the resin may be a silica resin. The particle size of the resin may be, for example, between about 100 μm to about 800 μm (e.g., about 100 μm to about 700 μm, about 100 μm to about 600 μm, about 100 μm to about 500 μm, about 100 μm to about 400 μm, about 100 μm to about 300 μm, about 100 μm to about 200 μm, about 200 μm to about 800 μm, about 300 μm to about 800 μm, about 400 μm to about 800 μm, about 500 μm to about 800 μm, about 600 μm to about 800 μm, about 700 μm to about 800 μm, about 200 μm to about 600 μm).

For example, the particle size of the resin may be between about 300 μm and about 600 μm (e.g., about 300 μm to about 550 μm, about 300 μm to about 500 μm, about 300 μm to about 450 μm, about 300 μm to about 400 μm, about 300 μm to about 350 μm, about 350 μm to about 600 μm, about 400 μm to about 600 μm, about 450 μm to about 600 μm, about 500 μm to about 600 μm, about 550 μm to about 600 μm, or about 400 μm and about 500 μm). The resin may require an activation step. The activation step may be, for example, drying of the resin prior to use.

The resin may have a bulk density of between 0.1 g/mL and 0.75 g/mL (e.g., between 0.1 g/mL and 0.5 g/mL, 0.1 g/mL and 0.25 g/mL, 0.2 g/mL and 0.75 g/mL, 0.5 g/mL and 0.75 g/mL. 0. g/mL and 0.75 g/mL, or 0.3 g/mL and 0.5 g/mL). For example, the resin may have a bulk density of between 0.25 g/mL and 0.5 g/mL (e.g., between 0.25 g/mL and 0.4 g/mL, 0.25 g/mL and 0.3 g/mL, 0.3 g/mL and 0.5 g/mL, 0.4 g/mL and 0.5 g/mL, or 0.3 g/mL and 0.4 g/mL). In some embodiments, the resin has a pore volume of between 0.1 mL/g and 1.5 mL/g (e.g., between 0.1 mL/g and 1.2 g/mL, 0.1 mL/g and 1 mL/g, 0.1 mL/g and 0.7 mL/g, 0.1 mL/g and 0.5 mL/g, 0.1 mL/g and 0.2 mL/g, 0.2 mL/g and 1.5 mL/g, 0.7 mL/g and 1.5 mL/g, 1 mL/g and 1.5 mL/g, 1.2 mL/g and 1.5 mL/g, or 0.5 mL/g and 1 mL/g). For example, the resin may have a pore volume of between 0.5 mL/g and 1 mL/g (e.g., 0.5 mL/g, 0.6 mL/g, 0.7 mL/g, 0.8 mL/g, 0.9 mL/g, or 1 mL/g). The resin may have an approximate water content of less than 1% w/w. In some embodiments, the resin has an approximate water content of between 2% w/w and 9% w/w (e.g., between 2% w/w and 6% w/w, 2% w/w and 5% w/w, 2% w/w and 4% w/w, 3% w/w and 9% w/w, 5% w/W and 9% w/w, 7% w/w and 9% w/w, or 4% w/w and 6% w/w). For example, the resin has an approximate water content of between 4.5% w/w to 6.5% w/w (e.g., 4.5% w/w, 4.6% w/w, 4.7% w/w, 4.8% w/w, 4.9% w/w, 5% w/w, 5.1% w/w, 5.2% w/w, 5.3% w/w, 5.4% w/w, 5.5% w/w, 5.6% w/w, 5.7% w/w, 5.8% w/W, 5.9% w/w, 6% w/w, 6.1% w/w, 6.2% w/w, 6.3% w/w, 6.4% w/w, or 6.5% w/w).

The resin may be pre-wet prior to the isoprenoid composition contacting the resin. In the pre-wetting step, the resin may be fully wetted by passing a solved over the resin. For example, the resin may be pre-wet by passing between 1 bed volume (BV) and 4 BV (e.g., 1 BV, 2 BV, 3 BV, or 4 BV) of solvent over the resin. In some embodiments, the pre-wetting step includes passing a solvent over the resin in an amount of 2 BV. The pre-wetting step may be performed by passing the solvent over the resin such that it is passed over with a minimum residence time on the column of at least 10 min. The solvent may be passed over the resin with a maximum downflow superficial velocity of between 0.5 cm/min and 5 cm/min (e.g., between 0.5 cm/min and 5 cm/min, 1 cm/min and 5 cm/min, 2 cm/min and 5 cm/min, 3 cm/min and 5 cm/min, 4 cm/min and 5 cm/min, 0.5 cm/min and 4 cm/min, 0.5 cm/min and 2 cm/min, or 1 cm/min and 3 cm/min) in the pre-wetting step. For example, the solvent may be passed over the resin with a maximum downflow superficial velocity of between 1 cm/min and 4 cm/min (e.g., between 1 cm/min and 3 cm/min, 1 cm/min and 2 cm/min, 2 cm/min and 4 cm/min, 3 cm/min and 4 cm/min, or 2 cm/min and 3 cm/min) in the pre-wetting step. In some embodiments, the solvent is passed over the resin with a maximum upflow superficial velocity of between 0.05 cm/min and 5 cm/min (e.g., between 0.5 cm/min and 5 cm/min, 1 cm/min and 5 cm/min, 2 cm/min and 5 cm/min, 3 cm/min and 5 cm/min, 4 cm/min and 5 cm/min, 0.5 cm/min and 4 cm/min, 0.5 cm/min and 2 cm/min, 1 cm/min and 3 cm/min, 0.05 cm/min and 3 cm/min, 0.05 cm/min and 1 cm/min, or 0.05 cm/min and 0.1 cm/min). For example, the solvent may be passed over the resin with a maximum upflow superficial velocity of between 0.1 cm/min and 3 cm/min (e.g., between 1 cm/min and 3 cm/min, 1 cm/min and 2 cm/min, 0.1 cm/min and 2 cm/min, 0.1 cm/min and 1 cm/min, or 2 cm/min and 3 cm/min). In the pre-wetting step, the resin may be fully wetted by passing the farnesene composition over the resin.

Following the pre-wetting step, the farnesene composition may be exposed to the resin. In some embodiments, the resin is not subjected to a pre-wetting step prior to the farnesene composition being exposed to the resin. The farnesene composition may be exposed to the resin with a minimum residence time on the resin of at least 10 min. The farnesene composition may be exposed to the resin with a maximum downflow superficial velocity of between 1 cm/min and 15 cm/min (e.g., between 1 cm/min and 10 cm/min, 1 cm/min and 5 cm/min, 1 cm/min and 3 cm/min, 3 cm/min and 15 cm/min, 5 cm/min and 15 cm/min, 10 cm/min and 15 cm/min, or 5 cm/min and 10 cm/min). For example, the farnesene composition may be exposed to the resin with a maximum downflow superficial velocity of between 5 cm/min and 11 cm/min (e.g., 5 cm/min, 6 cm/min, 7 cm/min, 8 cm/min, 9 cm/min, 10 cm/min, or 11 cm/min). The farnesene composition may be exposed to the resin with a maximum upflow superficial velocity of between 0.1 cm/min and 10 cm/min (e.g., between 0.1 cm/min and 8 cm/min, 0.1 cm/min and 6 cm/min, 0.1 cm/min and 4 cm/min, 0.1 cm/min and 1 cm/min, 1 cm/min and 10 cm/min, 3 cm/min and 10 cm/min, 5 cm/min and 10 cm/min, 8 cm/min and 10 cm/min, 4 cm/min and 8 cm/min, or 2 cm/min and 6 cm/min). For example, the farnesene composition may be exposed to the resin with a maximum upflow superficial velocity of between 1 cm/min and 5 cm/min (e.g., 1 cm/min, 2 cm/min, 3 cm/min, 4 cm/min, or 5 cm/min).

The chromatography step may include regenerating the resin. Regeneration of the resin may include adding a polar solvent to the resin; removing the polar solvent from the resin; heating the resin; and cooling the resin. The regeneration step may include adding polar solvent to the resin in an amount of between 1 BV and 10 BV (e.g., 1 BV, 2 BV, 3 BV, 4 BV, 5 BV, 6 BV, 7 BV, 8 BV, 9 BV, or 10 BV). For example, the polar solvent is added to the resin in an amount of between 2 BV and 6 BV (e.g., 2 BV, 3 BV, 4 BV, 5 BV, or 6 BV). In some embodiments, the polar solvent is added to the resin in an amount of about 4 BV. In the regeneration step, the resin may be heated. The resin may be heated to a temperature of between 100° C. and 200° C. (e.g., between 100° C. and 180° C., 100° C. and 160° C., 100° C. and 140° C., 100° C. and 120° C., 120° C. and 200° C., 150° C. and 200° C., 170° C. and 200° C., 140° C. and 180° C., or 120° C. and 160° C.). For example, the resin is heated to a temperature of about 150° C. Following heating the resin, the resin may be cooled to room temperature. The resin may be regenerated with any polar solvent; for example, the polar solvent may be methanol or isopropanol.

The chromatography step may be performed under $N_2$.

Purity of Isolated Isoprenoids

Disclosed herein are compositions that include a high purity isoprenoid recovered from an isoprenoid composition. The concentration of the isoprenoid relative to the total amount of the isoprenoid and the one or more impurities in the composition may be, for example, from 95% (w/w) to 100% (w/w) or more, e.g., 95% (w/w), 95.5% (w/w), 96% (w/w), 96.5% (w/w), 97% (w/w), 97.5% (w/w), 98% (w/w), 98.5% (w/w), 99% (w/w), 99.5% (w/w) or 100% (w/w), or more. In some embodiments, the isoprenoid relative to the total amount of the isoprenoid and the one or more impurities in the composition is from 98% (w/w) to 100% (w/w) (e.g., 98% (w/w), 98.1% (w/w), 98.2 wt, 98.3% (w/w), 98.4% (w/w), 98.5% (w/w), 98.6% (w/w), 98.7% (w/w), 98.8% (w/w), 98.9% (w/w), 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). In some embodiments, the isoprenoid relative to the total amount of the isoprenoid and the one or more impurities in the composition is from 99% (w/w) to 100% (w/w) (e.g., 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). For example, the concentration of isoprenoid relative to the total amount of the isoprenoid and the one or more impurities in the composition may be from about 99.5% (w/w) to about 100% (w/w), or more, for example, about 99.5% (w/w), 99.6% (w/w), 99.7% (w/w), 99.8% (w/w), 99.9% (w/w), or 100% (w/w).

In some embodiments, the isoprenoid concentration relative to the total amount of the isoprenoid and the one or more impurities can be up to 100% (w/w), such as up to 100% (w/w), 99% (w/w), 98% (w/w), 97% (w/w), 96% (w/w), 95% (w/w), 94% (w/w), 93% (w/w), 92% (w/w), 91% (w/w), or 90% (w/w). In some embodiments, the isoprenoid concentration relative to the total amount of the isoprenoid and the one or more impurities may be greater than 95% (w/w), e.g., greater than 95% (w/w), greater than 96% (w/w), greater than 97% (w/w), greater than 98% (w/w), greater than 99% (w/w), greater than 99.1% (w/w), greater than 99.2% (w/w), greater than 99.3% (w/w), greater than 99.4% (w/w), greater than 99.5% (w/w), greater than 99.6% (w/w), greater than 99.7% (w/w), greater than 99.8% (w/w), or greater than 99.9% (w/w).

In some embodiments, an isoprenoid-containing composition of the disclosure may contain isoprenoid and one or more impurities, such that the concentration of the one or more impurities relative to the total amount of isoprenoid and the one or more impurities is from about 0.1% (w/w) to about 0.5% (w/w), such as about 0.1% (w/w), 0.2% (w/w), 0.3% (w/w), 0.4% (w/w), or 0.5% (w/w). In some embodiments, the concentration of the one or more impurities relative to the total amount of the isoprenoid and the one or more impurities is less than 0.5% (w/w), e.g., less than 0.4% (w/w), less than 0.3% (w/w), less than 0.2% (w/w), or less than 0.1% (w/w). In some embodiments, the concentration of the one or more impurities relative to the total amount of the isoprenoid and the one or more impurities is about 0.1% (w/w), about 0.2% (w/w), about 0.3% (w/w), about 0.4% (w/w), or about 0.5% (w/w).

Also disclosed herein are compositions that specifically include a high purity composition of the isoprenoid farnesene which is recovered from a farnesene composition. The concentration of the farnesene relative to the total amount of the farnesene and the one or more impurities in the composition may be, for example, from 95% (w/w) to 100% (w/w) or more, e.g., 95% (w/w), 95.5% (w/w), 96% (w/w), 96.5% (w/w), 97% (w/w), 97.5% (w/w), 98% (w/w), 98.5% (w/w), 99% (w/w), 99.5% (w/w) or 100% (w/w), or more. In some embodiments, the farnesene relative to the total amount of the farnesene and the one or more impurities in the composition is from 98% (w/w) to 100% (w/w) (e.g., 98% (w/w), 98.1% (w/w), 98.2 wt, 98.3% (w/w), 98.4% (w/w), 98.5% (w/w), 98.6% (w/w), 98.7% (w/w), 98.8% (w/w), 98.9% (w/w), 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). In some embodiments, the farnesene relative to the total amount of the farnesene and the one or more impurities in the composition is from 99% (w/w) to 100% (w/w) (e.g., 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). For example, the concentration of farnesene relative to the total amount of the farnesene and the one or more impurities in the composition may be from about 99.5% (w/w) to about 100% (w/w), or more, for example, about 99.5% (w/w), 99.6% (w/w), 99.7% (w/w), 99.8% (w/w), 99.9% (w/w), or 100% (w/w).

The isolated isoprenoid of the present disclosure may be purified from an isoprenoid composition with a purity of from about 95% (w/w) to about 100% (w/w) (e.g., 95% (w/w) to 100% (w/w) or more, e.g., 95% (w/w), 95.5% (w/w), 96% (w/w), 96.5% (w/w), 97% (w/w), 97.5% (w/w), 98% (w/w), 98.5% (w/w), 99% (w/w), 99.5% (w/w) or 100% (w/w), or more). The isoprenoid may be purified from the isoprenoid composition with a purity of from about 98% (w/w) to about 100% (w/w) (e.g., 98% (w/w), 98.1% (w/w), 98.2 wt, 98.3% (w/w), 98.4% (w/w), 98.5% (w/w), 98.6% (w/w), 98.7% (w/w), 98.8% (w/w), 98.9% (w/w), 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). For example, the isoprenoid is purified from the isoprenoid composition with a purity of from about 99% (w/w) to about 100% (w/w) (e.g., 99% (w/w), 99.1% (w/w), 99.2% (w/w), 99.3% (w/w), 99.4% (w/w), 99.5% (w/w), 99.6% (w/w), 99.7% (w/w), 99.8% (w/w), 99.9% (w/w), or 100% (w/w)). In some embodiments, the isoprenoid is purified from the isoprenoid composition with a purity of from about 99.5% (w/w) to about 100% (w/w), or more, for example, about 99.5% (w/w), 99.6% (w/w), 99.7% (w/w), 99.8% (w/w), 99.9% (w/w), or 100% (w/w).

In some embodiments, the farnesene concentration relative to the total amount of the farnesene and the one or more impurities can be up to 100% (w/w), such as up to 100% (w/w), 99% (w/w), 98% (w/w), 97% (w/w), 96% (w/w), 95% (w/w), 94% (w/w), 93% (w/w), 92% (w/w), 91% (w/w), or 90% (w/w). In some embodiments, the farnesene concentration relative to the total amount of the farnesene and the one or more impurities may be greater than 95% (w/w), e.g., greater than 95% (w/w), greater than 96% (w/w), greater than 97% (w/w), greater than 98% (w/w), greater than 99% (w/w), greater than 99.1% (w/w), greater than 99.2% (w/w), greater than 99.3% (w/w), greater than 99.4% (w/w), greater than 99.5% (w/w), greater than 99.6% (w/w), greater than 99.7% (w/w), greater than 99.8% (w/w), or greater than 99.9% (w/w).

In some embodiments, a farnesene-containing composition of the disclosure may contain farnesene and one or more impurities, such that the concentration of the one or more impurities relative to the total amount of farnesene is from about 0.1% (w/w) to about 0.5% (w/w), such as about 0.1% (w/w), 0.2% (w/w), 0.3% (w/w), 0.4% (w/w), or 0.5% (w/w). In some embodiments, the concentration of the one or more impurities relative to the total amount of the farnesene and the one or more impurities is less than 0.5% (w/w), e.g., less than 0.4% (w/w), less than 0.3% (w/w), less than 0.2% (w/w), or less than 0.1% (w/w). In some embodiments, the concentration of the one or more impurities relative to the total amount of the farnesene and the one or more impurities is about 0.1% (w/w), about 0.2% (w/w), about 0.3% (w/w), about 0.4% (w/w), or about 0.5% (w/w).

The impurities within the composition comprising the isolated high purity isoprenoid may include, for example, polar impurities. In some embodiments, the composition comprises high purity isoprenoid and one or more impurities. The one or more impurities may include, for example, farnesol and farnesene epoxide.

The composition may comprises impurities comprising farnesol. The farnesol may have a concentration of between 0 mg/ml and 1 g/L (e.g., between 0.2 g/L and 1 g/L, 0.4 g/L and 1 g/L, 0.6 g/L, 0.6 g/L and 1 g/L, 0.8 g/L and 1 g/L, 0 mg/mL, and 0.8 g/L, 0 mg/mL and 0.6 g/L, 0 mg/mL and 0.4 g/L, 0 mg/ml and 0.2 g/L, 0.4 g/L and 0.6 g/L, or 0.2 g/L and 0.8 g/L). For example, the concentration of farnesol may be between 0 mg/L and 600 mg/L (e.g., between 0 mg/ml and 500 mg/mL, 0 mg/mL and 400 mg/mL, 0 mg/mL and 300 mg/mL, 0 mg/mL and 200 mg/mL, 0 mg/mL and 100 mg/mL, 100 mg/mL and 600 mg/mL, 200 mg/mL and 600 mg/mL, 300 mg/mL and 600 mg/mL, 400 mg/mL and 600 mg/mL, 500 mg/ml and 600 mg/mL, 200 mg/mL and 400 mg/mL, or 300 mg/mL and 500 mg/mL). In some embodiments, the concentration of farnesol is less than 500 mg/L in the composition comprising the high-purity isoprenoid. The composition may include the isoprenoid and one or more impurities including farnesene epoxide. The farnesene epoxide may be present in the composition at a concentration of between 0 mg/mL and 500 mg/L (e.g., between 0 mg/ml and 400 mg/mL, 0 mg/mL and 300 mg/mL, 0 mg/mL and 200 mg/mL, 0 mg/ml and 100 mg/mL, 100 mg/mL and 500 mg/mL, 200 mg/mL and 500 mg/mL, 300 mg/ml and 500 mg/mL, 400 mg/mL and 500 mg/mL, 200 mg/mL and 400 mg/mL, or 100 mg/mL and 300 mg/mL). The composition may include the isoprenoid and a farnesene epoxide impurity having a concentration of between 0 mg/L and 200 mg/L (e.g., between 0 mg/L and 150 mg/L, 0 mg/L and 100 mg/L, 0 mg/L and 50 mg/L, 50 mg/L and 200 mg/L, 100 mg/L and 200 mg/L, 150 mg/L and 200 mg/L, 20 mg/L and 100 mg/L, or 50 mg/L and 150 mg/L). For example, the concentration of farnesene epoxide may be less than 150 mg/L.

Culture and Fermentation Methods

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The isoprenoids described herein may, in some embodiments, be isolated from a host cell capable of producing an isoprenoid. The host cell culture may be performed in a suitable culture medium in a suitable container, including but not limited to a cell culture plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag Gmbh & Co. KDaA, Weinheim, Germany.

In some embodiments, the culture medium is any culture medium in which a microorganism capable of producing a heterologous product can subsist, i.e., maintain growth and viability. In some embodiments, the culture medium is an aqueous medium comprising assimilable carbon, nitrogen and phosphate sources. Such a medium can also include appropriate salts, minerals, metals, and other nutrients. In some embodiments, the carbon source and each of the essential cell nutrients are added incrementally or continuously to the fermentation medium, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable medium for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

Host Cell Strains

In some embodiments of the present disclosure, the host cell is a yeast cell. Yeast cells useful in conjunction with the compositions and methods described herein include yeast that have been deposited with microorganism depositories (e.g. IFO, ATCC, etc.), such as those that belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkera, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, chizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the strain is *Saccharomyces cerevisiae, Pichia pastoris, Schizosaccharomyces pombe, Dekkera bruxellensis, Kluyveromyces lactis* (previously called *Saccharomyces lactis*), *Kluyveromyces marxianus, Arxula adeninivorans*, or *Hansenula* polymorphs (now known as *Pichia angusta*). In some embodiments, the host microbe is a strain of the genus *Candida*, such as *Candida lipolytica, Candida guilliermondii, Candida krusei, Candida pseudotropicalis*, or *Candida utilis*.

In some embodiments, the host cell is *Saccharomyces cerevisiae*. *Saccharomyces cerevisiae* strains suitable for cultivation to produce isoprenoid as disclosed herein include, but are not limited to, Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, CEN.PK, CEN.PK2, and AL-1. In some embodiments, the host cell is a strain of *Saccharomyces cerevisiae* selected from the group consisting of PE-2, CAT-1, VR-1, BG-1, CR-1, and SA-1. In certain aspects, the strain of *Saccharomyces cerevisiae* is PE-2. In certain embodiments, the strain of *Saccharomyces cerevisiae* is CAT-1. In some aspects, the strain of *Saccharomyces cerevisiae* is BG-1.

In some embodiments, the host cell is *Kluyveromyces marxianus*. *Kluyveromyces marxianus* can provide several advantages for industrial production, including high temperature tolerance, acid tolerance, native uptake of lactose, and rapid growth rate. Beneficially, this yeast has sufficient genetic similarity to *Saccharomyces cerevisiae* such that similar or identical promoters and codon optimized genes can be used among the two yeast species.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Isolation of High Purity Farnesene from Distilled Farnesene

Farnesene, a $C_{15}$ hydrocarbon, was produced using fermentation, and isolated using centrifugation and distillation. This distilled farnesene was typically 97% (w/w) pure and contained about 1% of oxygenate impurities that needed to be removed to ppm levels before it could be used as a monomer in polymerization reactions. An adsorption-based purification process was used to purify the distilled farnesene such that the farnesene had greater than 99% w/w purity. The process used to purify farnesene included an adsorption step through a basic alumina bed followed by bed draining using pressurized nitrogen gas, in-situ regeneration utilizing methanol solvent, and in-situ adsorbent activation.

These experiments were conducted on a 15 cm long, 2.5 cm diameter glass column plumbed through a skid that used a dual-headed pump, a pneumatic valve system, and variable nitrogen flow.

The adsorbent material used was ESM-20 (28×48 mesh) Basic Alumina from ASM Catalysts, LLC. Adsorbent properties are presented in Table 1 and Table 2. Langmuir parameters were calculated for ESM-20 Basic Alumina, using pure component equilibrium data, obtained in the laboratory at 22° C.

TABLE 1

ESM-20 Basic Alumina properties

| Property | Sorbent |
|---|---|
| Bulk density (g/mL) | 0.57 |
| Pore volume (mL/g) | 0.73* |
| Particle size distribution (microns) | 300-600 |
| Approximate water content (%) | ~5-6% |

*The pore volume was calculated using known density and void fraction data.

TABLE 2

ESM-20 Basic Alumina Langmuir isotherm parameters

| Impurity | Wmax (mg impurity/g adsorbent) | K (mL/mg impurity) |
|---|---|---|
| Farnesol | 204.08 | 8.249 |
| Epoxide | 66.225 | 3.134 |

The specifications for the alumina treated farnesene product are shown in Table 3.

TABLE 3

Exemplary specification for high purity farnesene

| Test Description | Specification Limits Minimum | Maximum | Unit of Measurement |
|---|---|---|---|
| Farnesene Assay | 97.5 | | wt % |
| Total Farnesol* | | 500 | mg/L |
| Total Farnesene Epoxide* | | 150 | mg/L |
| Water by KF | | 100 | Mg/L |
| Color | Report | | APHA Units |
| Total acid number (TAN) | | 0.015 | mg KOH/g |
| TBC Inhibitor | 30 | 100 | ppm |

*Combinations that conform to the following overall oxygenates specification are acceptable: 500 < [Total farnesol, mg/L] + 3.3 [Total Farnesene Epoxides, mg/L]

Feed Impurity Profile

Table 4 presents the feed impurity profile variability which was used as the starting material to isolate the high purity farnesene.

TABLE 4

Typical column feed composition

| Compound | Average | Standard deviation | Units |
|---|---|---|---|
| Farnesene | 97.6 | 0.5 | Wt % |
| Farnesene | 98.0 | 0.1 | Area % |
| Total Farnesol isomers | 0.71 | 0.06 | Area % |
| Total Farnesene Epoxides | 0.022 | 0.004 | Area % |
| Water | 35 | 8 | mg/L |
| Total Acid Number | 0.055 | 0.015 | mg KOH/g |
| 4-tert-butylcatechol (TBC) | 142 | 47 | mg/L |
| Color | 5 | 1 | APHA Units |

Process Steps
Adsorbent Loading

Alumina was loaded to the column and mass of alumina charge was recorded. The equipment was pressure tested to 50 psig using dry nitrogen
Pre-Wetting The valves/equipment were reconfigured as needed to start pumping distilled farnesene. The pump was set to the flow rate and the flow of the distilled farnesene was started. 2 BV of material was flowed over the column and the material was collected as product. The process samples were checked for farnesol and epoxide concentrations and then stabilized with an antioxidant.

The adsorption process was operated at ambient temperature, without active heating or cooling. The wetting step was mildly exothermic, and a maximum temperature rise of ~7° C. was observed in the laboratory scale column, based on the skin temperatures recorded on a 2.5×15 cm stainless steel column. This initial exotherm subsided once the first bed volume of feed was processed, and the column was fully wetted. Consistent with laboratory experience, a maximum transient temperature rise of ~8° C. was recorded at the 300 L scale, based on the temperature difference between the process inlet and outlet lines. No temperature measurements were made within the alumina bed, either in the laboratory, or at pilot scale.

The maximum superficial velocity, and the corresponding mass flowrate for both the pre-wetting and adsorption steps were determined by the minimum residence time requirement, the bed fluidization limit (applicable in upflow operation), and the particle attrition limit (applicable in downflow operation). In particular, feed should be processed more slowly during the first bed volume (pre-wetting), when the column was not yet filled with liquid. The following design limits were observed during the operation of this process:

TABLE 5

Adsorption Process Design Limits

| Minimum Residence Time (min) | 10 |
|---|---|
| Maximum Downflow Superficial Velocity (cm/min) | 8.2 |
| Maximum Downflow Superficial Velocity During Initial Wetting (cm/min) | 2.1 |
| Maximum Upflow Superficial Velocity (cm/min) | 3.6 |
| Maximum Upflow Superficial Velocity During Initial Wetting (cm/min) | 0.9 |

Adsorption

The pump was set to the flow rate and the distilled farnesene began to be pumped. The process samples were checked for farnesol and epoxide concentrations after each BV. The material was collected as a product and was stabilized with antioxidant.
Farnesene Hold Up Recovery The equipment was reconfigured as needed to switch to dry nitrogen gas. The dry nitrogen gas was set to the specified flow rate. The liquid was blown down by flowing nitrogen for an amount of time. The blown down material was collected in a separate container from the product. The process samples were collected for farnesol and epoxide concentrations after each BV. The material was collected as a product and stabilized with antioxidant.
Hold Up Recovery (Draining)

To maximize yield, the farnesene that was held up in the void space of the column was recovered by draining the column while blowing dry nitrogen through it. The recovered farnesene could either be blended into product, if it was sufficiently close to being on-spec, or it could be recycled to the feed tank for future reprocessing. The total bed porosity was approximately 86%. The expected fraction of recovered hold up was 43-48%, based on interparticle void space of the bed. This was consistent with what was observed in the laboratory. Five (5) to seven (7) bed volumes of on-spec product were typically obtained on the 15 cm laboratory column depending on the feed impurity concentration profile. In combination with a 40% holdup recovery, this implied an overall process yield of 92%. The number of bed volumes of product obtained, and the corresponding yield, was expected to be even higher on larger columns which had improved bed utilization, relative to lab scale columns.

Alumina Regeneration

The alumina bed was regenerated. The valves/equipment were reconfigured as needed to start pumping methanol. The pump was set to the flow rate specified and the methanol was started flowing. The specified amount of material was flowed over the column. Conventional temperature and pressure swing adsorption cycles were not suitable for this application since farnesene is non-volatile and reacts to form significant quantities of dimers and polymers within minutes at fairly low temperatures (<100 C). Instead, a hybrid chemical swing/temperature swing adsorption approach was used to regenerate the alumina bed. Methanol was used as the solvent of choice because of its low cost, high volatility and high affinity for alumina. C15 impurities were displaced by flowing methanol through the bed countercurrent to farnesene (methanol in downflow) at ambient temperature. The effluent methanol was captured and stored for later purification. Next, the bed was drained using pressurized nitrogen, to remove the easily accessible liquid holdup (typically 50-60% of total MeOH holdup). The methanol that remained in the bed after draining was by heating the bed in-situ, to 150° C. or higher temperature. The methanol vapor effluent was condensed and combined with the liquid effluent from the previous step. Finally, the bed was cooled back down to ambient temperature in preparation for the next adsorption cycle.

Bed regeneration has been demonstrated at laboratory scale over 5 regeneration passes. Four bed volumes of methanol composed of >90% recycled solvent per pass were used to regenerate the bed on each pass.

Solvent Recycle

Spent methanol effluent from the bed regeneration step were purified and recycled. In the laboratory, methanol was purified using single step evaporation at 43° C. and 150 torr vacuum. These conditions were selected to achieve per pass methanol recovery >90%, at a distilled methanol purity of 99.9%, while maintaining evaporator temperature as low as possible to mitigate against polymer formation and possible fouling in the evaporator.

Alternate evaporator conditions of 350 torr, 60° C. have been estimated using process modeling tools. These conditions should yield distilled methanol at comparable yield and purity and can be operated using a condenser temperature of 35° C.

In-Situ Activation

The equipment was reconfigured as needed to have nitrogen flow travel through a condenser system. To ensure that the condenser achieved the desired temperature, the cooling water was set to the flow rate and desired temperature. The dry nitrogen gas was set to the desired flow rate. A flow of steam was flowed to the jacket wrapped around the column at the desired flow rate and temperature. The temperature of the column was monitored to ensure that it achieved the desired temperature. The condensed material was collected in separate containers from the product.

Laboratory Results

Laboratory scale purification of distilled farnesene feed was completed using ESM-20 (28×48 mesh) Basic Alumina. The glass laboratory column was 2.5 cm ID×15 cm. The laboratory column did not have built in distributors and was run in upflow to ensure even radial distribution of feed across the alumina bed. The operating conditions used in the lab are summarized in Table 6 below.

TABLE 6

Operation conditions for laboratory runs on 2.5 ID × 15 cm glass column

| Parameter | Adsorption | Units |
| --- | --- | --- |
| Inner diameter, ID = | 2.5 | Cm |
| Column height, H = | 15 | Cm |
| Mass flow rate, g/min | 6.0 | g/min |
| Liquid density, rfene = | 0.824 | g/mL |
| Cross-sectional area, A = | 4.909 | cm^2 |
| Column Volume, Vcolumn = | 73.63 | cm^3 |
| Volumetric flow rate, Q = | 7.282 | mL/min |
| Superficial velocity, Us = | 1.483 | cm/min |
| Interstitial velocity, Ui = | 1.730 | cm/min |
| Residence time, t = | 8.671 | Min |
| # of Bed Volumes = | 6 | BV |

Six (6) adsorption passes, and five (5) regenerations were completed in succession, on one (1) packed bed of alumina using one (1) lot of farnesene. Four bed volumes of virgin methanol were utilized for the first bed regeneration, and recycled methanol was used for the later regeneration passes. 90-93% of the spent methanol was recovered on each evaporator pass, and GC analysis of the methanol distillate confirmed its C15 content to be lower than 0.1%. The capacity loss observed after the first regeneration (see Table 7) is typical of previous laboratory data and is believed to be due to the crushing/attrition of the bed caused by introduction of ~10 psi nitrogen during draining. After the first regeneration, bed capacity remained basically constant, to within the limits of experimental error. The laboratory experiment was terminated after a net recycle rate of 75% had been demonstrated. Based on the data obtained, it should be possible to continue regenerating the bed well beyond five (5) regeneration passes. Over multiple experiments, the typical high purity farnesene included the components of Table 7 and FIG. 1.

TABLE 7

Molar capacity per regeneration pass. The final row represents a mole balance including the expected capacity loss due to chemisorbed acids.

| Solvent Recovery | Pass ID | R0A1 | R1A2 | R2A3 | R3A4 | R4A5 | R5A6 |
| --- | --- | --- | --- | --- | --- | --- | --- |
| Total Moles Adsorbed | | 0.018895 | 0.01821 | 0.018147 | 0.017767 | 0.0176135 | 0.017818 |

TABLE 7-continued

Molar capacity per regeneration pass. The final row represents a mole balance
including the expected capacity loss due to chemisorbed acids.

| Solvent Recovery | Pass ID | R0A1 | R1A2 | R2A3 | R3A4 | R4A5 | R5A6 |
|---|---|---|---|---|---|---|---|
| % Removal vs. Previous Pass | | | 96.37% | 99.66% | 97.91% | 99.13% | 101.16% |
| Mass Balance Including Capacity Loss via TAN | | | 96.59% | 99.88% | 98.13% | 99.37% | 101.40% |

Product Typical Impurity Profile

Typical impurity profiles for the chromatography treated farnesene product are shown in the table below and in FIG. 1.

TABLE 8

Typical composition of product (chromatography treated farnesene")

| Compound | Average | Standard deviation | Units |
|---|---|---|---|
| Farnesene | 97.5 | 0.8 | Wt % |
| Farnesene | 98.0 | 0.3 | Area % |
| Total Farnesol isomers | <LOQ | | mg/L |
| Total Farnesene Epoxides | 8 | | mg/L |
| Water | 36 | 40 | mg/L |
| Total Acid Number | 0.011 | 0.003 | mg KOH/g |
| Color APHA | 5 | 1 | |

Example 2. Purification of Farnesene Using Various Resins

Chromatography was used to purify a farnesene composition using various resin types.

Alumina Resins

Figure 2B:
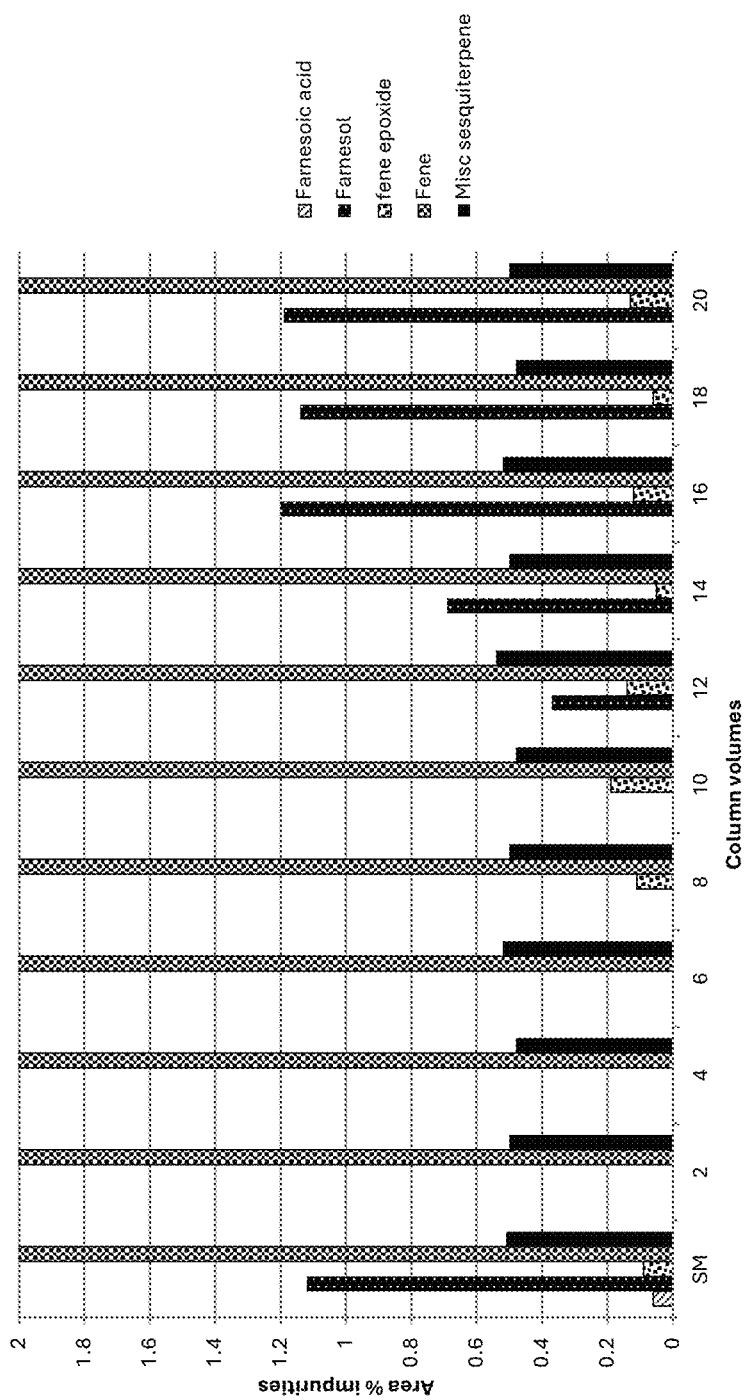
Figure 2C:
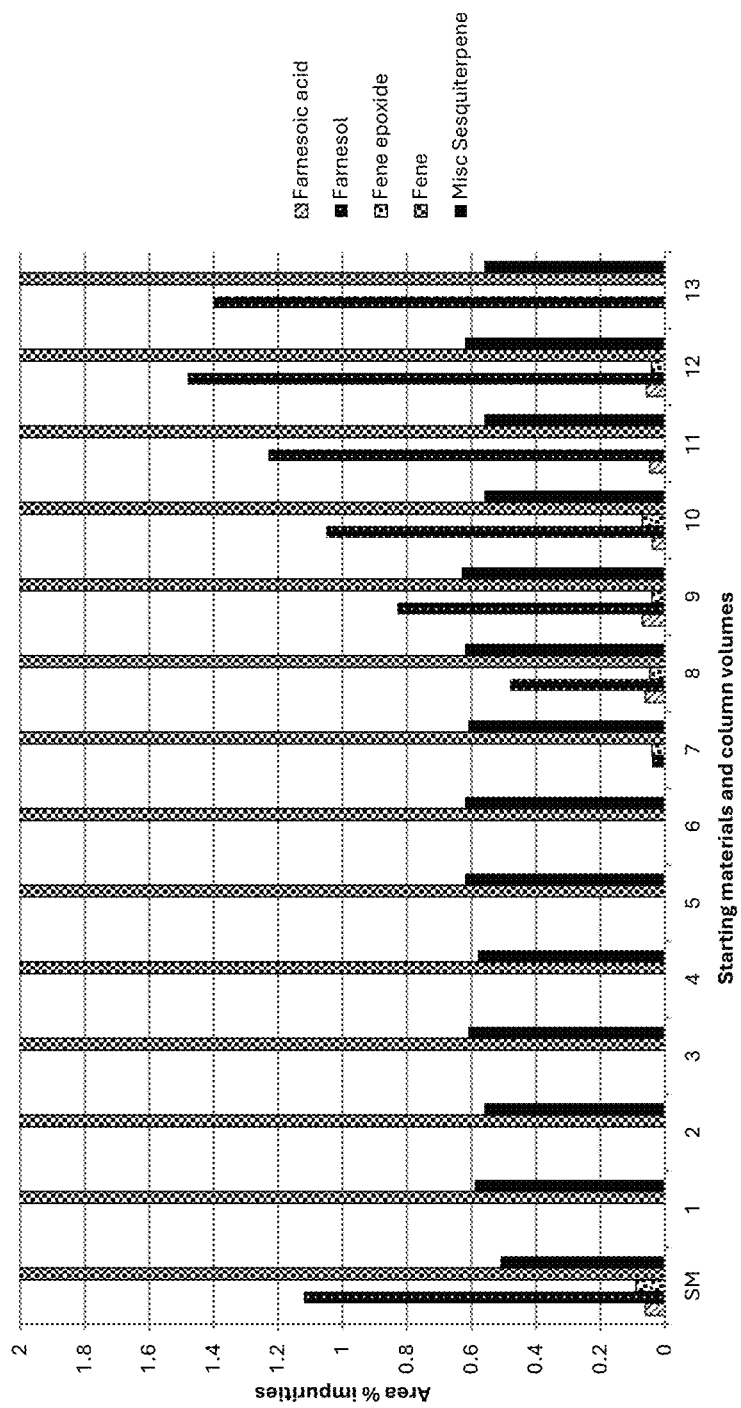

The farnesene was purified in the same manner as described in Example 1 using: (1) basic alumina resin from Sorbent Technology, (2) basic alumina resin from Sigma Aldrich, or (3) Activity Super 1 activated alumina from Sorbent Technology. The purity of the resulting farnesene was characterized and the concentration of various impurities including farnesene epoxide, farnesol and farnesoic acid were measured for alumina stripping performed using basic alumina from Sorbent Technology (FIG. 2A), basic alumina from Sigma Aldrich (FIG. 2B), and Activity Super I activated alumina from Sorbent Technology (FIG. 2C), the measurements of which are summarized below in Tables 9-12.

TABLE 9

Characterization of Farnesene Purification with
Basic Alumina from Sorbent Technology

| | Farnesoic acid Area % | Farnesol Area % | Farnesene epoxide Area % | Farnesene Area % |
|---|---|---|---|---|
| Starting Material | 0.06 | 1.12 | 0.09 | 97.81 |
| 2 | 0 | 0 | 0 | 99.37 |
| 4 | 0 | 0 | 0 | 99.49 |
| 6 | 0 | 0 | 0 | 99.52 |
| 8 | 0 | 0 | 0 | 99.52 |
| 10 | 0 | 0.16 | 0.06 | 99.28 |
| 12 | 0.05 | 0.66 | 0.11 | 98.52 |
| 14 | 0.04 | 0.96 | 0.09 | 97.88 |
| 16 | 0.03 | 1.11 | 0.09 | 98.04 |
| 18 | 0.04 | 1.18 | 0.1 | 97.89 |
| 20 | 0 | 1.2 | 0.14 | 98.01 |

TABLE 10

Characterization of Farnesene Purification with
Basic Alumina from Sigma Aldrich

| | Farnesoic acid Area % | Farnesol Area % | Farnesene epoxide Area % | Farnesene Area % |
|---|---|---|---|---|
| Starting Material | 0.06 | 1.12 | 0.09 | 97.81 |
| 2 | 0 | 0 | 0 | 99.33 |
| 4 | 0 | 0 | 0 | 99.53 |
| 6 | 0 | 0 | 0 | 99.48 |
| 8 | 0 | 0 | 0.11 | 99.39 |
| 10 | 0 | 0 | 0.19 | 99.21 |
| 12 | 0 | 0.37 | 0.14 | 98.85 |
| 14 | 0 | 0.69 | 0.05 | 97.86 |
| 16 | 0 | 1.2 | 0.12 | 97.94 |
| 18 | 0 | 1.14 | 0.06 | 98.2 |
| 20 | 0 | 1.19 | 0.13 | 97.95 |

TABLE 11

Characterization of Farnesene Purification with Activity
Super I Activated Alumina from Sorbent Technology

| | Farnesoic acid Area % | Farnesol Area % | Farnesene epoxide Area % | Farnesene Area % |
|---|---|---|---|---|
| Starting Material | 0.06 | 1.12 | 0.09 | 97.81 |
| 1 | 0 | 0 | 0 | 99.11 |
| 2 | 0 | 0 | 0 | 99.43 |
| 3 | 0 | 0 | 0 | 99.38 |
| 4 | 0 | 0 | 0 | 99.42 |
| 5 | 0 | 0 | 0 | 99.38 |
| 6 | 0 | 0 | 0 | 99.35 |
| 7 | 0 | 0.04 | 0.04 | 99.24 |
| 8 | 0.06 | 0.48 | 0.047 | 98.66 |
| 9 | 0.07 | 0.83 | 0.04 | 98.06 |
| 10 | 0.04 | 1.05 | 0.07 | 97.96 |

TABLE 11-continued

Characterization of Farnesene Purification with Activity
Super I Activated Alumina from Sorbent Technology

| | Farnesoic acid Area % | Farnesol Area % | Farnesene epoxide Area % | Farnesene Area % |
|---|---|---|---|---|
| 11 | 0.047 | 1.23 | | 97.83 |
| 12 | 0.057 | 1.48 | 0.041 | 97.4 |
| 13 | | 1.4 | | 97.76 |

Alumina and Silica Resins

The farnesene purity was characterized after chromatography performed using Sigma Aldrich aluminum oxide resin in comparison to a silica gel Merck resin. The experiments were performed on a column (1.5 cm×11.2 cm, 19.8 mL) which was dry packed in the same manner as described in Example 1. Crude farnesene filtered through basic alumina (9 bed volume) before breakthrough of farnesol (0.1%) and no acidic species (e.g., farnesoic acid) were detected. Crude farnesene filtered through silica gel with farnesol and farnesoic acid breakthrough occurring after 5 CV and other acid species were observed after 4 CV. At 1.5 L scale, crude farnesene filtered through basic alumina (7 bed volume) before breakthrough of farnesol occurred and no acidic species (e.g., farnesoic acid) was detected.

Example 3. Alumina Treatment of Cadinane to Remove Polar Impurities

Alumina Treatment of Cadinane Spiked with Sandalwood to Remove Santalols

A column (1 cm ID×14 cm, 11 mL BV) was dry packed with Sorbent Technologies Alumina Basic, Activation I adsorbent. Cadinane (194.0 g) was mixed with sandalwood oil containing santalene and santalols (15.4 g). The cadinane was purified in the same manner as described above in Example 1. The mixture was analyzed by GC-MS and the santalols area purity was found to be 1.2 area %. The cadinane-Sandalwood mixture was loaded on to the alumina column at a flow rate of 0.7-0.9 mL/min (3-4 BV/hr). Eluant was collected in 1 BV portions (11 mL) and analyzed by GC-MS to determine the reduction in santalols levels.

The breakthrough data of santalols after alumina column treatment was determined. The alumina column was able to reduce santalols from over 12000 ppm to below detection level for the first three bed volumes as shown in FIG. 3 and Table 12.

TABLE 12

GC-MS data of santalols after alumina column treatment

| BV | Santalene & Cadinane Stereoisomers (GC-MS Area %) | Santalols (GC-MS Area %) |
|---|---|---|
| Cadinane Feed | 98.7 | 1.2 |
| 1 | 99.8 | 0.0 |
| 2 | 99.7 | 0.0 |
| 3 | 99.8 | 0.0 |
| 4 | 98.8 | 1.0 |
| 5 | 98.9 | 0.9 |
| 6 | 98.9 | 0.9 |

Alumina Treatment of Cadinane Spiked with Hexahydrofarnesoic Acid (HHFA)

A column (1 cm ID×14 cm, 11 mL BV) was dry packed with Sorbent Technologies Alumina Basic, Activation I adsorbent. The cadinane was purified in the same manner as described above in Example 1. Cadinane (198.5 g) was mixed with HHFA (13 g) to create 211 g of feed. The mixture was analyzed by GC-MS and the HHFA area purity was found to be 1.1 area %. The cadinane-HHFA mixture was loaded on to the alumina column at a flow rate of 0.7-0.9 mL/min (3-4 BV/hr). Eluant was collected in 1 BV portions and analyzed by GC-MS to determine the reduction in HHFA levels.

Figure 4:
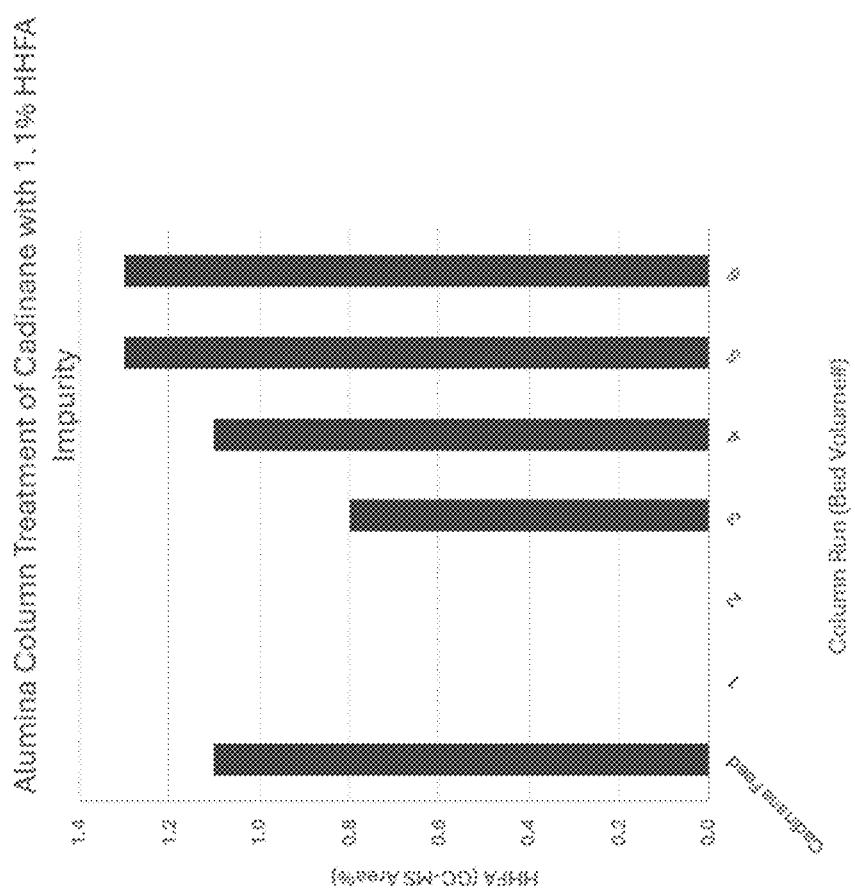
FIG. 4 is a graph showing the breakthrough data of hexahydrofarnesoic acid (HHFA) after alumina column treatment where no HHFA was observed in the first two BVs.

No HHFA was observed in the first two BVs, which demonstrated the utility of alumina treatment to remove polar impurities present at over 11000 ppm as shown in FIG. 4 and Table 13.

TABLE 13

GC-MS data of HHFA after alumina column treatment

| BV | Cadinane Stereoisomers (GC-MS Area %) | HHFA (GC-MS Area %) |
|---|---|---|
| Cadinane Feed | 98.7 | 1.1 |
| 1 | 99.8 | 0.0 |
| 2 | 99.8 | 0.0 |
| 3 | 99.1 | 0.8 |
| 4 | 98.7 | 1.1 |
| 5 | 98.6 | 1.3 |
| 6 | 98.5 | 1.3 |

Example 4. Acid Treatment of Farnesene

This experiment was performed to test whether acid treatment could successfully remove impurities from both distilled and crude farnesene in order to obtain a high purity farnesene product, similar to the high purity farnesene product which resulted from the methods described in Examples 1-3 above. However, acid treatment of both the crude and distilled farnesene resulted in a number of challenges, described below, which ultimately made purification of the farnesene with an acid treatment less effective than the preceding Examples.

To determine the feasibility of the acid treatment process for the production of high purity farnesene, a DOE (design of experiment) was performed to evaluate the effect of temperature, time, and phosphoric acid loadings. The responses measured were in terms of gas chromatograph (GC) area percent farnesene, farnesol, dimer, farnesene epoxide, total acid number (TAN), and color (Saybalt). The distilled farnesene used in these experiments contained ~8000 ppm farnesol and 250 ppm farnesene epoxide. Farnesene was typically added to a round bottom flask and the liquid was mixed at 340 rpm. The acid was then added, and the suspension was brought to temperature. Aliquots of the acid treated farnesene were taken at 30 minute intervals and centrifuged to remove the acid phase. Tert-butyl cathecol (TBC, 100 ppm) was immediately added to the separated farnesene phase as a stabilizer to reduce oxidation.

Figures 6A, 6B:
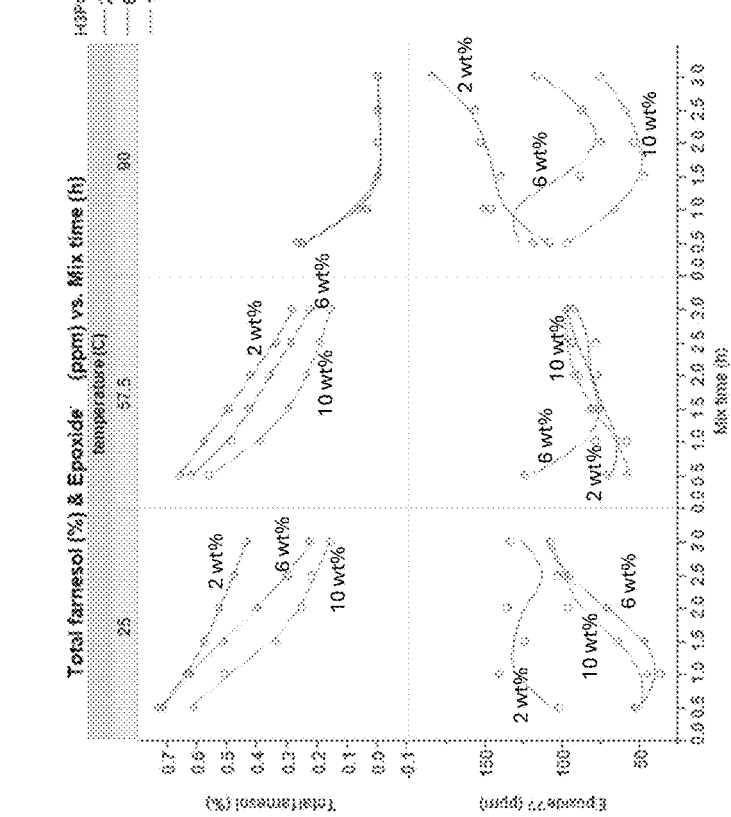
FIG. 6A and FIG. 6B are graphs showing the change in: (i) farnesol and farnesene epoxide concentration (FIG. 6A) and (ii) farnesene and farnesene dimer (FIG. 6B) in distilled farnesene at 25° C., 57.5° C., and 90° C. and acid concentration of 2 wt %, 6 wt %, and 10 wt % over time.

Farnesol and farnesene epoxides were readily removed from farnesene by mixing with as low as 2 wt % $H_3PO_4$ at 80-90° C. for 1.5-2 hr (FIG. 6A). The data describing the results of the epoxide purification were confounded due to the creation of co-eluting impurities during the reaction. Experiments in which the acid treated farnesene was spiked with the farnesene epoxide indicated that the farnesene epoxide was removed from the farnesene in less than 1 hr. Farnesene losses were however increased at elevated temperature due to the formation of farnesene dimer. This increase in dimer was accompanied by a decrease in the farnesene area purity (FIG. 6B). The dimer content could be kept to less than 1 wt % by reacting farnesene with acid at 80° C. for no longer than 3 hr.

Figure 7:
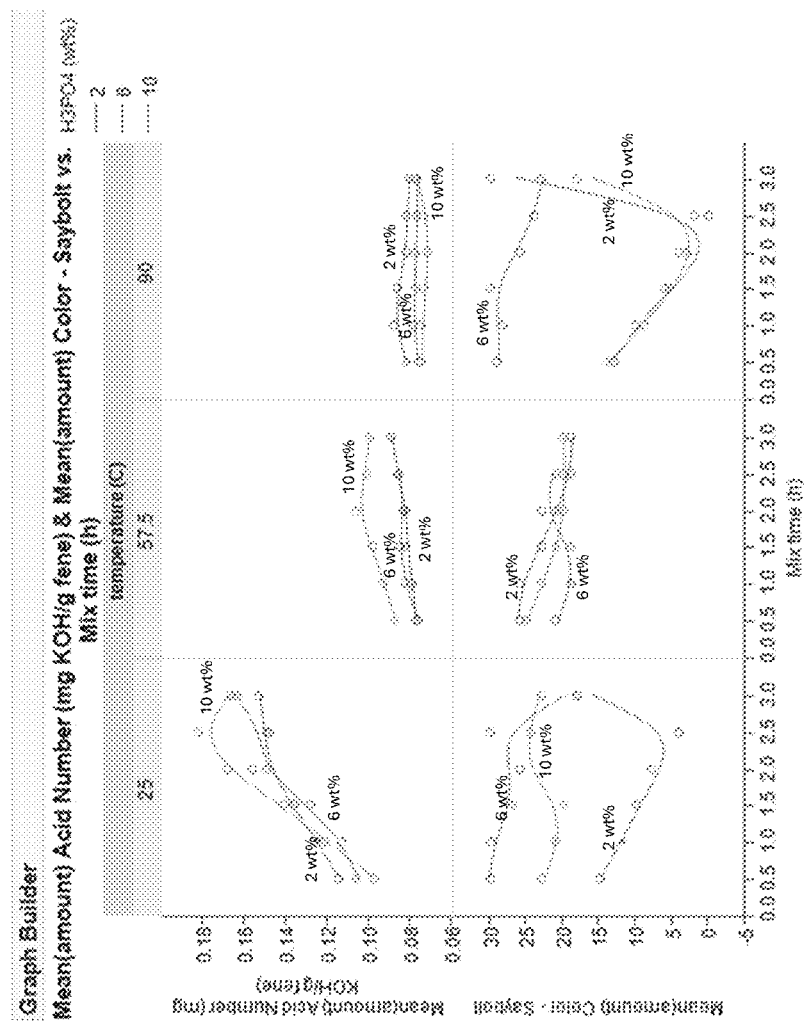
FIG. 7 is a graph showing solution color of distilled farnesene upon treatment with acid at concentrations of 2 wt %, 6 wt %, and 10 wt % at 25° C., 57.5° C., and 90° C. and over time.

The acid content of the treated farnesene was observed to be consistently lower at higher temperature regardless of the acid usage (FIG. 7). The resulting farnesene had a pale yellow color compared to the colorless distilled farnesene. None of the factors tested showed correlation to the color of the treated material. Several by-products were observed in the acid treated farnesene. Liquid chromatography-mass spectrometry (LCMS) analyses indicated that two of these compounds were potentially cyclized $C_{15}$ oxygenates, while other impurities were products of dehydration and isomerization of alcohols, epoxides and farnesene.

Using the data from the performed experiments, a predictive model was created using the response surface methodology (RSM). The JMP prediction profiler was used to determine the most appropriate conditions for producing acid treated farnesene that met defined specifications. The defined specifications included: (1) farnesene having a minimum area percent purity of 97 wt %, (2) a maximum of 1000 ppm farnesol content, (3) dimer levels no greater than 1%. Using these defined specifications, two scale up experiments were performed. The first scale up trial was performed on a ~8 L scale at 80° C. with 4 wt % $H_3PO_4$. The suspension was mixed for 2.5 hr and then cooled to room temperature. The farnesene was decanted, and a portion was stabilized by TBC and submitted for analysis. The overall mass yield recovery for the unpolished acid treated farnesene was 99.3 wt %. The material produced met or exceeded the desired specifications, indicating the model that was used to determine the appropriate conditions to meet the desired specifications was very predictive (Table 14). It was noted that the resulting material had a pale yellow color and a TAN of 0.095 mg KOH/g farnesene. There was a desire to produce a second scale up trial of acid-treated material with lower TAN and reduced color for testing of the adsorption bed.

TABLE 14

Process and analytical data for acid treated distilled farnesene

| Parameters | Distilled farnesene (starting material) | 1$^{st}$ Scale Up Trial (unpolished) | 2$^{nd}$ Scale Up Trial (polished) |
|---|---|---|---|
| Mass Yield (%) | | 99.8 | 98.3 |
| Fene wt. % | 97.4 | 96.7 | |
| Fene area % | 97.8 | 97.5 | 97.1 |
| Color | 25* | 11 | 13 |
| TAN (mg KOH/g) | 0.075 | 0.097 | 0.065 |
| Farnesol (ppm) | 7850 | 115 | 226 |
| Epoxide (ppm) | 200 | 0 | 0 |
| Dimer (%) | 0.2 | 0.9 | 0.8 |
| KF (ppm) | 50 | 63 | 100 |

*A Saybalt color of 25 is typical is typical for distilled farnesene

The model was updated with color data and used to predict the best conditions for scale-up. The distilled farnesene was treated with 6.9 wt % $H_3PO_4$ at 77° C. for 3 hr. The resulting suspension was cooled to room temperature and the farnesene layer recovered and washed with water to remove acidic species. The washed organic layer was mixed with dilute NaOH, to neutralize any remaining acid components, and subsequently washed a second time with water. The farnesene was then dried with anhydrous magnesium sulfate. The overall mass yield for the polished farnesene was 98.3 wt %. The TAN and water content of the farnesene was noticeably lower than the unpolished material. However, a pale yellow color was still evident. The colored component could be removed using an adsorbent such as activated charcoal and clay. The envisioned process for making high purity material from distilled farnesene would therefore require one or more additional polishing steps to address both color and acidity.

Acid treatment of crude farnesene was viewed as an attractive option to mitigate the overall purification cost, since oxygenates and heavy component such as glycerides and surfactants could be removed in a single step, thus eliminating the need for a distillation step. To validate this approach, a design of experiment was carried out with crude farnesene. The custom designed approach was performed in a similar manner to when distilled farnesene was used, as described above. The factors evaluated were time, temperature, and $H_3PO_4$ loadings. Crude farnesene was mixed at room temperature, $H_3PO_4$ was added, and the suspension was brought to temperature. Aliquots were taken at 0.5, 1, 2 and 4 hr time points. The aliquots were centrifuged, and the farnesene layer recovered and tested.

Figure 8A:
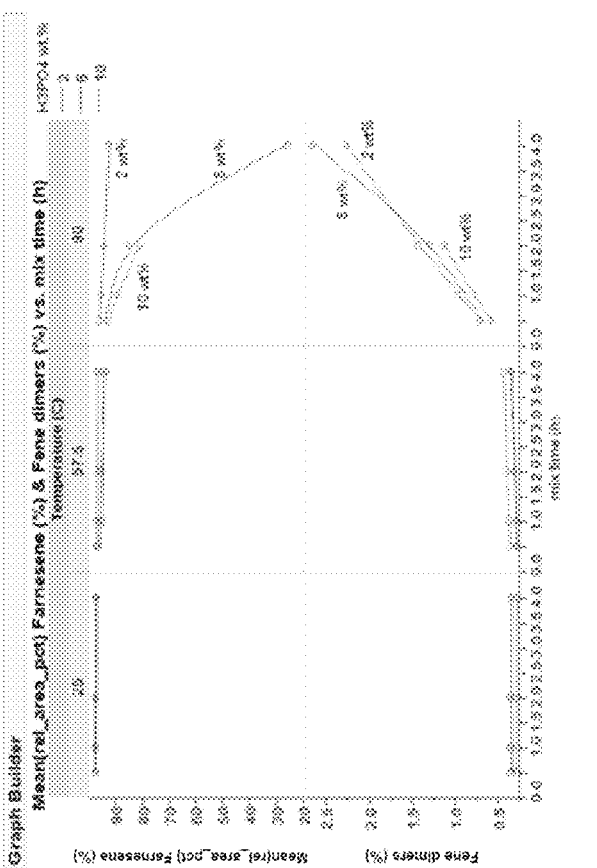
FIG. 8A and FIG. 8B are graphs showing the amount of: (i) (FIG. 8A) and (ii) dimer formation and farnesene loss during the treatment of crude farnesene (FIG. 8B) with $H_3PO_4$.
Figure 8B:
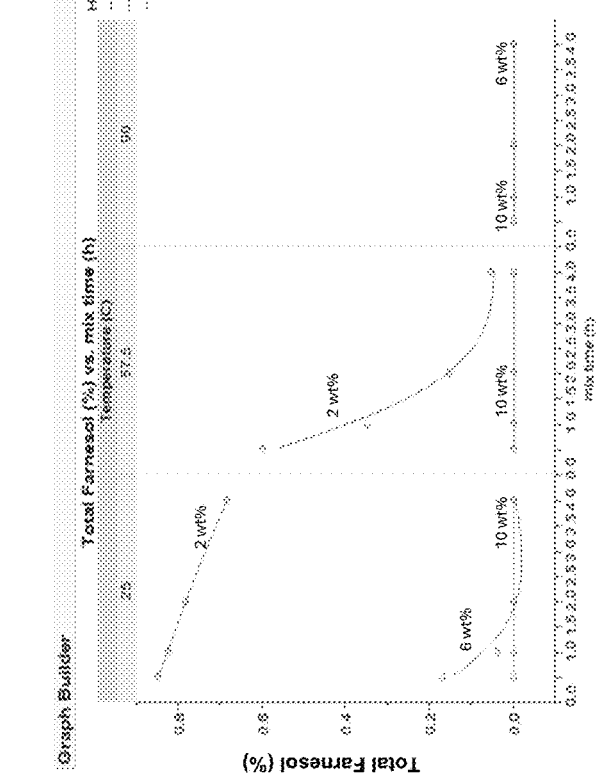

Farnesol and farnesene epoxides were effectively removed from crude farnesene by mixing with 6 wt % $H_3PO_4$ at room temperature. Lower acid usages resulted in a single farnesene layer and the formation of a viscous, brown gum ("acid phase") on the walls of the reaction vessel. A minimum of 4 wt % acid was required to prevent formation of the brown gum and to keep the acid phase fully suspended. Dimer formation was negligible at room temperature, however significant dimer formation was observed at higher temperatures. A concomitant reduction in farnesene area percent was observed (FIG. 8A). The weight percent assay for elected samples of acid treated crude farnesene was lower than the 97 wt % specification. A rapid decrease in the weight percent assay of farnesene was observed with increasing mix time (Table 15). Isomerization of farnesene and other sesquiterpenes rose considerably at 57° C. and 90° C. (FIG. 8B). Isomerization of farnesene was predominantly responsible for the low purity of farnesene observed when assayed at all temperatures. It should be noted that the low farnesene purity (20 wt %) at the 4 hr time point at 90° C. was due to a temperature excursion.

TABLE 15

Selected results from the acid treatment of crude farnesene at 25 ° C.

| $H_3PO_4$ wt. % | Mix time (hr) | Farnesene area purity (%) | Farnesene wt. purity (/%) | KF (ppm) |
|---|---|---|---|---|
| 6 | 0.5 | 97.97 | 95.61 | |
| 6 | 1 | 98.08 | 94.97 | 306.7 |
| 6 | 2 | 97.98 | 94.01 | |
| 6 | 4 | 97.81 | 89.47 | 89.8 |
| 10 | 0.5 | 97.84 | 91.89 | |
| 10 | 1 | 97.42 | 85.3 | 67 |
| 10 | 2 | 97.42 | 79.2 | |
| 10 | 4 | 97.12 | 70.56 | 41.5 |

Several attempts were made to reduce the acidity and color of the acid treated crude farnesene by washing with water and base. These attempts resulted in the formation of a milky, emulsified farnesene layer. The emulsion remained unbroken after centrifugation at 5000 rpm. When the emulsified farnesene was mixed with 8 wt % clay, a very pale yellow transparent farnesene phase resulted. As a result, the farnesene losses associated with the clay treatment (estimated at 8 wt %) resulted in an acid treatment process that would not be competitive with the processes for farnesene purification described in herewith. The formation of isomerization products on oxygenates during acid treatment made the process described in this example less appealing for removal of oxygenates from farnesene.

CONCLUSION

Farnesol and farnesene epoxides may be removed more readily from crude farnesene compared to distilled farnesene at much lower temperatures. However, the crude farnesene had a tendency to isomerize during the process, which resulted in a lower purity of farnesene, as measured by the wt % percent of farnesene assayed. Additionally, polishing of the crude farnesene resulted in the formation of an emulsion, which required additional process steps. Lastly, several by-products were formed during the acid treatment of both crude and distilled farnesene, which made purification of the farnesene with an acid treatment undesirable.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

Numbered Embodiment

The invention disclosed herein is also represented by the following non-limiting, enumerated paragraphs

[1] A method of purifying farnesene, the method comprising:
  (a) providing a farnesene composition; and
  (b) purifying the farnesene from the farnesene composition of (a) by way of chromatography.

[2] The method of paragraph [1], wherein the farnesene composition comprises farnesene and one or more impurities.

[3] The method of paragraph [2], wherein the one or more impurities comprise one or more polar impurities, optionally wherein the one or more polar impurities comprise farnesoic acid, farnesol, farnesene oxide, farnesene epoxide, a fatty acid, a sterol, hexahydrofarnesoic acid (HHFA), santalene, or santalol.

[4] The method of paragraph [2] or [3], wherein the farnesene composition has a concentration of one or more impurities of between 1 ppm and 15,000 ppm.

[5] The method of paragraph [4], wherein the farnesene composition has a concentration of one or more impurities of between 1000 ppm and 12,000 ppm.

[6] The method of paragraph [4], wherein the farnesene composition has a concentration of one or more impurities of between 100 ppm and 1,000 ppm.

[7] The method of any one of paragraphs [1]-[6], wherein 4-tert butylcatechol is added to the farnesene composition.

[8] The method of paragraph [7], wherein the 4-tert butylcatechol is added to the farnesene composition to a concentration of from 50 ppm to 150 ppm, optionally wherein the 4-tert butylcatechol is added to the farnesene composition to a concentration of about 100 ppm.

[9] The method of any one of paragraphs [1]-[8], wherein the farnesene composition is not treated with phosphoric acid prior to the purifying step of (b), wherein the farnesene composition is not treated with an acid prior to the purifying step of (b).

[10] The method of paragraph [9], wherein the farnesene composition is not treated with an acid prior to the purifying step of (b).

[11] The method of any one of paragraphs [1]-[10], wherein the chromatography comprises:
  (a) pre-wetting a resin;
  (b) exposing the farnesene composition to the resin; and
  (c) collecting the farnesene from the resin.

[12] The method of paragraph [11], wherein the resin comprises aluminum oxide.

[13] The method of paragraph [12], wherein the aluminum oxide is basic aluminum oxide.

[14] The method of paragraph [12], wherein the aluminum oxide is acidic aluminum oxide.

[15] The method of paragraph [12], wherein the aluminum oxide is neutral aluminum oxide.

[16] The method of paragraph [11], wherein the resin comprises silica.

[17] The method of any one of paragraphs [12]-[16], wherein the resin has a bulk density of between 0.1 g/mL and 0.75 g/mL.

[18] The method of paragraph [17], wherein the resin has a bulk density of between 0.25 g/mL and 0.5 g/mL.

[19] The method of any one of paragraphs [11]-[18], wherein the resin has a pore volume of between 0.1 mL/g and 1.5 mL/g.

[20] The method of paragraph [19], wherein the resin has a pore volume of between 0.5 mL/g and 1 mL/g.

[21] The method of any one of paragraphs [11]-[20], wherein the resin has a particle distribution size of between 25 μm and 800 μm, optionally, wherein the resin has a particle distribution size of between 100 μm and 800 μm.

[22] The method of paragraph [21], wherein the resin has a particle distribution size of between 300 μm and 600 μm.

[23] The method of any one of paragraphs [11]-[22], wherein the resin has an approximate water content of between 0.01% w/w and 9% w/w.

[24] The method of paragraph [23], wherein the resin has an approximate water content of between 4.5% w/w to 6.5% w/w.

[25] The method of any one of paragraphs [11]-[24], wherein the pre-wetting step comprises fully wetting the resin by passing a solvent over the resin.

[26] The method of paragraph [25], wherein the pre-wetting step comprises passing the solvent over the resin in an amount of 1 bed volumes (BV) to 4 BV.

[27] The method of paragraph [26], wherein the pre-wetting step comprises passing the solvent over the resin in an amount of 2 BV.

[28] The method of any one of paragraphs [25]-[27], wherein the solvent is passed over the resin with a minimum residence time on the column of at least 10 min in the pre-wetting step.

[29] The method of any one of paragraphs [25]-[28], wherein the solvent is passed over the resin with a maximum downflow superficial velocity of between 0.5 cm/min and 5 cm/min in the pre-wetting step.

[30] The method of paragraph [29], wherein the solvent is passed over the resin with a maximum downflow superficial velocity of between 1 cm/min and 4 cm/min in the pre-wetting step.

[31] The method of any one of paragraphs [25]-[30], wherein the solvent is passed over the resin with a maximum upflow superficial velocity of between 0.05 cm/min and 5 cm/min.

[32] The method of paragraph [31], wherein the solvent is passed over the resin with a maximum upflow superficial velocity of between 0.1 cm/min and 3 cm/min.

[33] The method of any one of paragraphs [11]-[30], wherein the farnesene composition is exposed to the resin following the pre-wetting step.

[34] The method of paragraph [33], wherein the farnesene composition is exposed to the resin with a minimum residence time on the resin of at least 10 min.

[35] The method of paragraph or [34], wherein the farnesene composition is exposed to the resin with a maximum downflow superficial velocity of between 1 cm/min and 15 cm/min.

[36] The method of paragraph [35], wherein the farnesene composition is exposed to the resin with a maximum downflow superficial velocity of between 5 cm/min and 11 cm/min.

[37] The method of any one of paragraphs [33]-[36], wherein the farnesene composition is exposed to the resin with a maximum upflow superficial velocity of between 0.1 cm/min and 10 cm/min.

[38] The method of paragraph [37], wherein the farnesene composition is exposed to the resin with a maximum upflow superficial velocity of between 1 cm/min and 5 cm/min.

[39] The method of any one of paragraphs [11]-[38], wherein the steps (a) through (c) are repeated from 2 to 20 times.

[40] The method of paragraph [39], wherein the steps (a) through (c) are repeated from 2 to 20 times.

[41] The method of paragraph [40], wherein the steps (a) through (c) are repeated from 2 to 10 times.

[42] The method of paragraph [41], wherein the steps (a) through (c) are repeated 6 times.

[43] The method of paragraph [41], wherein the steps (a) through (c) are repeated from 2 to 4 times.

[44] The method of any one of paragraphs [11]-[43], wherein the resin is regenerated following the collection of the farnesene from the resin in step (c).

[45] The method of paragraph [44], wherein the resin is regenerated by:
  (a) adding a polar solvent to the resin;
  (b) removing the polar solvent from the resin;
  (c) heating the resin; and
  (d) cooling the resin.

[46] The method of paragraph [45], wherein step (a) is performed by adding the polar solvent to the resin in an amount of between 1 BV and 10 BV.

[47] The method of paragraph [46], wherein the polar solvent is added to the resin in an amount of between 2 BV and 6 BV.

[48] The method of paragraph [47], wherein the polar solvent is added to the resin in an amount of about 4 BV.

[49] The method of any one of paragraphs [45]-[48], wherein step (c) is performed by heating the resin to a temperature of between 100° C. and 200° C.

[50] The method of paragraph [49], wherein the resin is heated to a temperature of about 150° C.

[51] The method of any one of paragraphs [45]-[50], wherein the cooling of step (d) is performed by cooling the resin to room temperature.

[52] The method of any one of paragraphs [1]-[51], wherein the chromatography is performed under $N_2$.

[53] The method of any one of paragraphs [1]-[52], wherein the farnesene is purified from the farnesene composition with a purity of from about 95% (w/w) to about 100% (w/w).

[54] The method of paragraph [53], wherein the farnesene is purified from the farnesene composition with a purity of from about 98% (w/w) to about 100% (w/w).

[55] The method of paragraph [54], wherein the farnesene is purified from the farnesene composition with a purity of from about 99% (w/w) to about 100% (w/w).

[56] The method of paragraph [55], wherein the is purified from the farnesene composition with a purity of from about 99.5% (w/w) to about 100% (w/w).

[57] A composition comprising farnesene, wherein the composition is produced by the method of any one of paragraphs [1]-[56].

[58] The composition of paragraph [57], wherein the farnesene has a purity of from about 95% (w/w) to about 100% (w/w).

[59] The composition of paragraph [58], wherein the farnesene has a purity of from about 98% (w/w) to about 100% (w/w), optionally wherein the farnesene has a purity of from about 99% (w/w) to about 100% (w/w).

[60] The composition of paragraph [59], wherein the farnesene has a purity of from about 99.5% (w/w) to about 100% (w/w).

[61] The composition of any one of paragraphs [57]-[60], wherein the composition comprises one or more impurities comprising farnesoic acid, farnesol, farnesene oxide, farnesene epoxide, a fatty acid, a sterol, HHFA, santalene, or santalol.

[62] A composition comprising farnesene and one or more impurities, wherein the purity of the farnesene is from about 95% (w/w) to about 100% (w/w), and wherein the one or more impurities comprise farnesoic acid, farnesol, farnesene oxide, farnesene epoxide, a fatty acid, a sterol, HHFA, santalene, or santalol.

[63] The composition of paragraph or [62], wherein the composition comprises farnesol having a concentration of farnesol is between 0 mg/ml and 1 g/L.

[64] The composition of paragraph [63], wherein the concentration of farnesol is between 0 mg/L and 600 mg/L.

[65] The composition of paragraph [64], wherein the concentration of farnesol is less than 500 mg/L.

[66] The composition of any one of paragraphs [61]-[65], wherein the composition comprises farnesene epoxide having a concentration of farnesol is between 0 mg/ml and 500 mg/L.

[67] The composition of paragraph [66], wherein the concentration of farnesene epoxide is between 0 mg/L and 200 mg/L.

[68] The composition of paragraph [67], wherein the concentration of farnesene epoxide is less than 150 mg/L.

[69] A composition comprising farnesene and one or more carriers, diluents, or excipients, wherein the purity of the farnesene is from about 99.5% (w/w) to about 100% (w/w).

[70] The composition of paragraph [69], wherein the farnesene is present with one or more impurities, and wherein the one or more impurities is present in a concentration of about 0.5% (w/w) or less.

[71] The composition of paragraph [70], wherein the one or more impurities is present in a concentration of about 0.4% (w/w) or less, optionally wherein the one or more impurities is present in a concentration of about 0.3% (w/w) or less, optionally wherein the one or more impurities is present in a concentration of about 0.2% (w/w) or less, optionally wherein the one or more impurities is present in a concentration of about 0.1% (w/w) or less.

[72] The composition of paragraph or [71], wherein the one or more impurities comprise farnesoic acid, farnesol, farnesene oxide, farnesene epoxide, a fatty acid, a sterol, HHFA, santalene, or santalol.

[73] A method of purifying isoprenoid, the method comprising:
  (a) providing an isoprenoid composition; and
  (b) purifying the isoprenoid from the isoprenoid composition of (a) by way of chromatography.

[74] The method of paragraph [73], wherein the isoprenoid composition comprises isoprenoid and one or more impurities.

[75] The method of paragraph [74], wherein the one or more impurities comprise one or more polar impurities.

[76] The method of paragraph [75], wherein the one or more polar impurities comprise farnesoic acid, farnesol, farnesene oxide, farnesene epoxide, a fatty acid, a sterol, HHFA, santalene, or santalol.

[77] The method of any one of paragraphs [74]-[76], wherein the isoprenoid composition has a concentration of one or more impurities of between 1 ppm and 15,000 ppm.

[78] The method of paragraph [77], wherein the isoprenoid composition has a concentration of one or more impurities of between 1000 ppm and 12,000 ppm.

[79] The method of paragraph [77], wherein the isoprenoid composition has a concentration of one or more impurities of between 100 ppm and 1,000 ppm.

[80] The method of any one of paragraphs [73]-[79], wherein 4-tert butylcatechol is added to the isoprenoid composition.

[81] The method of paragraph [80], wherein the 4-tert butylcatechol is added to the isoprenoid composition to a concentration of from 50 ppm to 150 ppm, optionally wherein the 4-tert butylcatechol is added to the isoprenoid composition to a concentration of about 100 ppm.

[82] The method of any one of paragraphs [73]-[81], wherein the isoprenoid composition is not treated with phosphoric acid prior to the purifying step of (b).

[83] The method of paragraph [82], wherein the isoprenoid composition is not treated with an acid prior to the purifying step of (b).

[84] The method of any one of paragraphs [73]-[83], wherein the chromatography comprises:
  (a) pre-wetting a resin;
  (b) exposing the isoprenoid composition to the resin; and
  (c) collecting the isoprenoid from the resin.

[85] The method of paragraph [84], wherein the resin comprises aluminum oxide.

[86] The method of paragraph [85], wherein the aluminum oxide is basic aluminum oxide.

[87] The method of paragraph [85], wherein the aluminum oxide is acidic aluminum oxide.

[88] The method of paragraph [85], wherein the aluminum oxide is neutral aluminum oxide.

[89] The method of paragraph [84], wherein the resin comprises silica.

[90] The method of any one of paragraphs [84]-[89], wherein the resin has a bulk density of between 0.1 g/mL and 0.75 g/mL.

[91] The method of paragraph [90], wherein the resin has a bulk density of between 0.25 g/mL and 0.5 g/mL.

[92] The method of any one of paragraphs [84]-[91], wherein the resin has a pore volume of between 0.1 mL/g and 1.5 mL/g.

[93] The method of paragraph [92], wherein the resin has a pore volume of between 0.5 mL/g and 1 mL/g.

[94] The method of any one of paragraphs [84]-[93], wherein the resin has a particle distribution size of between 25 μm and 800 μm, optionally, wherein the resin has a particle distribution size of between 100 μm and 800 μm.

[95] The method of paragraph [94], wherein the resin has a particle distribution size of between 300 μm and 600 μm.

[96] The method of any one of paragraphs [84]-[95], wherein the resin has an approximate water content of between 2% (w/w) and 9% (w/w).

[97] The method of paragraph [96], wherein the resin has an approximate water content of between 4.5% (w/w) to 6.5% (w/w).

[98] The method of any one of paragraphs [84]-[97], wherein the pre-wetting step comprises fully wetting the resin by passing a solvent over the resin.

[99] The method of paragraph [98], wherein the pre-wetting step comprises passing the solvent over the resin in an amount of 1 BV to 4 BV.

[100] The method of paragraph [99], wherein the pre-wetting step comprises passing the solvent over the resin in an amount of 2 BV.

[101] The method of any one of paragraphs [98]-[100], wherein the solvent is passed over the resin with a minimum residence time on the column of at least 10 min in the pre-wetting step.

[102] The method of any one of paragraphs [98]-[101], wherein the solvent is passed over the resin with a maximum downflow superficial velocity of between 0.5 cm/min and 5 cm/min in the pre-wetting step.

[103] The method of paragraph [102], wherein the solvent is passed over the resin with a maximum downflow superficial velocity of between 1 cm/min and 4 cm/min in the pre-wetting step.

[104] The method of any one of paragraphs [98]-[103], wherein the solvent is passed over the resin with a maximum upflow superficial velocity of between 0.05 cm/min and 5 cm/min.

[105] The method of paragraph [104], wherein the solvent is passed over the resin with a maximum upflow superficial velocity of between 0.1 cm/min and 3 cm/min.

[106] The method of any one of paragraphs [84]-[105], wherein the isoprenoid composition is exposed to the resin following the pre-wetting step.

[107] The method of paragraph [106], wherein the isoprenoid composition is exposed to the resin with a minimum residence time on the resin of at least 10 min.

[108] The method of paragraph or [107], wherein the isoprenoid composition is exposed to the resin with a maximum downflow superficial velocity of between 1 cm/min and 15 cm/min.

[109] The method of paragraph [108], wherein the isoprenoid composition is exposed to the resin with a maximum downflow superficial velocity of between 5 cm/min and 11 cm/min.

[110] The method of any one of paragraphs [106]-[109], wherein the isoprenoid composition is exposed to the resin with a maximum upflow superficial velocity of between 0.1 cm/min and 10 cm/min.

[111] The method of paragraph [110], wherein the isoprenoid composition is exposed to the resin with a maximum upflow superficial velocity of between 1 cm/min and 5 cm/min.

[112] The method of any one of paragraphs [80]-[109], wherein the steps (a) through (c) are repeated from 2 to 20 times.

[113] The method of paragraph [112], wherein the steps (a) through (c) are repeated from 2 to 20 times.

[114] The method of paragraph [113], wherein the steps (a) through (c) are repeated from 2 to 10 times.

[115] The method of paragraph [114], wherein the steps (a) through (c) are repeated 6 times.

[116] The method of any one of paragraphs [84]-[115], wherein the resin is regenerated following the collection of the isoprenoid from the resin in step (c).

[117] The method of paragraph [116], wherein the resin is regenerated by:
(a) adding a polar solvent to the resin;
(b) removing the polar solvent from the resin;
(c) heating the resin; and
(d) cooling the resin.

[118] The method of paragraph [117], wherein step (a) is performed by adding polar solvent to the resin in an amount of between 1 BV and 10 BV.

[119] The method of paragraph [118], wherein the polar solvent is added to the resin in an amount of between 2 BV and 6 BV.

[120] The method of paragraph [119], wherein the polar solvent is added to the resin in an amount of about 4 BV.

[121] The method of any one of paragraphs [117]-[120], wherein step (c) is performed by heating the resin to a temperature of between 100° C. and 200° C.

[122] The method of paragraph [121], wherein the resin is heated to a temperature of about 150° C.

[123] The method of any one of paragraphs [117]-[122], wherein the cooling of step (d) is performed by cooling the resin to room temperature.

[124] The method of any one of paragraphs [73]-[123], wherein the chromatography is performed under $N_2$.

[125] The method of any one of paragraphs [73]-[124], wherein the isoprenoid is a $C_5$-$C_{60}$ isoprenoid.

[126] The method of paragraph [125], wherein the isoprenoid is a $C_{15}$-$C_{60}$ isoprenoid.

[127] The method of any one of paragraphs [73]-[126], wherein the isoprenoid is a hemiterpenoid, monoterpenoid, sesquiterpenoid, diterpenoid, sesterterpenoid, triterpenoid, tetraterpenoid, or polyterpenoid.

[128] The method of claim [127], wherein the isoprenoid is a sesquiterpenoid.

[129] The method of paragraph [127], wherein the isoprenoid is a monoterpenoid.

[130] The method of any one of paragraphs [73]-[126], wherein the isoprenoid is a hemiterpene, monoterpene, sesquiterpene, diterpene, sesterterpene, triterpene, tetraterpene, or polyterpene.

[131] The method of paragraph wherein the isoprenoid is sesquiterpene.

[132] The method of any one of paragraphs [73]-[124], wherein the isoprenoid is abietadiene, amorphadiene, cadinane, carene, cuminaldehyde, eugenol, farnesene, geranial, isoprene, limonene, myrcene, ocimene, α-pinene, β-pinene, sabinene, γ-terpinene, terpinolene, thujone, neral, eucalyptol, citronellal, carvone, or valencene.

[133] The method of paragraph [132], wherein the isoprenoid is farnesene.

[134] The method of paragraph [132], wherein the isoprenoid is cadinane.

[135] The method of any one of paragraphs [73]-[134], wherein the isoprenoid is purified from the isoprenoid composition with a purity of from about 95% (w/w) to about 100% (w/w).

[136] The method of paragraph [135], wherein the isoprenoid is purified from the isoprenoid composition with a purity of from about 98% (w/w) to about 100% (w/w).

[137] The method of paragraph [136], wherein the isoprenoid is purified from the isoprenoid composition with a purity of from about 99% (w/w) to about 100% (w/w).

[138] The method of paragraph [137], wherein the is purified from the isoprenoid composition with a purity of from about 99.5% (w/w) to about 100% (w/w).

[139] A composition comprising an isoprenoid, wherein the composition is produced by the method of any one of paragraphs [73]-[138].

[140] The composition of paragraph [139], wherein the isoprenoid has a purity of from about 95% (w/w) to about 100% (w/w).

[141] The composition of paragraph [139], wherein the isoprenoid has a purity of from about 98% (w/w) to about 100% (w/w), optionally wherein the isoprenoid is purified from the isoprenoid composition with a purity of from about 99% (w/w) to about 100% (w/w).

[142] The composition of paragraph [141], wherein the isoprenoid has a purity of from about 99.5% (w/w) to about 100% (w/w).

[143] The composition of any one of paragraphs [139]-[142], wherein the composition comprises one or more impurities comprising farnesoic acid, farnesol, farnesene oxide, farnesene epoxide, a fatty acid, a sterol, HHFA, santalene, or santalol.

[144] A composition comprising an isoprenoid and one or more impurities, wherein the purity of the isoprenoid is from about 90% (w/w) to about 100% (w/w), and wherein the one or more impurities comprise farnesoic acid, farnesol, farnesene oxide, farnesene epoxide, a fatty acid, a sterol, HHFA, santalene, or santalol.

[145] The composition of paragraph or [144], wherein the composition comprises farnesol having a concentration of farnesol is between 0 mg/ml and 1 g/L.

[146] The composition of paragraph [145], wherein the concentration of farnesol is between 0 mg/L and 600 mg/L.

[147] The composition of paragraph [146], wherein the concentration of farnesol is less than 500 mg/L.

[148] The composition of any one of paragraphs [143]-[147], wherein the composition comprises farnesene epoxide having a concentration of farnesol is between 0 mg/ml and 500 mg/L.

[149] The composition of paragraph [148], wherein the concentration of farnesene epoxide is between 0 mg/L and 200 mg/L.

[150] The composition of paragraph [149], wherein the concentration of farnesene epoxide is less than 150 mg/L.

[151] A composition comprising an isoprenoid and one or more carriers, diluents, or excipients, wherein the purity of the isoprenoid is from about 99.5% (w/w) to about 100% (w/w).

[152] The composition of paragraph [151], wherein the isoprenoid is present with one or more impurities, and wherein the one or more impurities is present in a concentration of about 0.5% (w/w) or less.

[153] The composition of paragraph [152], wherein the one or more impurities is present in a concentration of about 0.4% (w/w) or less, optionally wherein the one or more impurities is present in a concentration of about 0.3% (w/w) or less, optionally wherein the one or more impurities is present in a concentration of about 0.2% (w/w) or less, optionally wherein the one or more impurities is present in a concentration of about 0.1% (w/w) or less.

[154] The composition of paragraph or [153], wherein the one or more impurities comprise farnesoic acid, farnesol, farnesene oxide, farnesene epoxide, a fatty acid, a sterol, HHFA, santalene, or santalol.

The invention claimed is:

1. A method of purifying farnesene, the method comprising:
   (a) providing a farnesene composition; and
   (b) purifying the farnesene from the farnesene composition of (a) by way of chromatography; wherein the chromatography comprises:
   (1) pre-wetting a resin;
   (2) exposing the farnesene composition to the resin; and
   (3) collecting the farnesene from the resin.

2. The method of claim 1, wherein the farnesene composition comprises farnesene and one or more impurities.

3. The method of claim 2, wherein the one or more impurities comprise one or more polar impurities comprising farnesoic acid, farnesol, farnesene oxide, farnesene epoxide, a fatty acid, a sterol, hexahydrofarnesoic acid (HHFA), santalene, or santalol.

4. The method of claim 2, wherein the farnesene composition has a concentration of one or more impurities of between 1 ppm and 15,000 ppm.

5. The method of claim 1, wherein the resin has:
   (a) a bulk density of between 0.1 g/mL and 0.75 g/ml;
   (b) a pore volume of between 0.1 mL/g and 1.5 mL/g;
   (c) a particle distribution size of between 25 μm and 800 μm; or
   (d) an approximate water content of between 0.01% w/w and 9% w/w.

6. The method of claim 1, wherein the farnesene composition is exposed to the resin following the pre-wetting step.

7. The method of claim 6, wherein the farnesene composition is exposed to the resin with a minimum residence time on the resin of at least 10 min with a maximum downflow superficial velocity of between 1 cm/min and 15 cm/min, and a maximum upflow superficial velocity of between 0.1 cm/min and 10 cm/min.

8. The method of claim 1, wherein the steps (a) through (c) are repeated from 2 to 20 times.

9. The method of claim 1, wherein the resin is regenerated following the collection of the farnesene from the resin in step (c).

10. The method of claim 9, wherein the resin is regenerated by:
    (a) adding a polar solvent to the resin;
    (b) removing the polar solvent from the resin;
    (c) heating the resin; and
    (d) cooling the resin.

11. The method of claim 1, wherein the farnesene is purified from the farnesene composition with a purity of from about 95% (w/w) to about 100% (w/w).

12. A method of purifying isoprenoid, the method comprising:
    (a) providing an isoprenoid composition; and
    (b) purifying the isoprenoid from the isoprenoid composition of (a) by way of chromatography; wherein the chromatography comprises:
    (1) pre-wetting a resin;
    (2) exposing the isoprenoid composition to the resin; and
    (3) collecting the isoprenoid from the resin.

13. The method of claim 12, wherein the isoprenoid composition comprises farnesene and one or more impurities.

14. The method of claim 13, wherein the one or more impurities comprise one or more polar impurities, optionally wherein the one or more polar impurities comprise farnesoic acid, farnesol, farnesene oxide, farnesene epoxide, a fatty acid, a sterol, HHFA, santalene, or santalol.

15. The method of claim 13, wherein the isoprenoid composition has a concentration of one or more impurities of between 1 ppm and 15,000 ppm.

16. The method of claim 12, wherein the resin has:
    (a) a bulk density of between 0.1 g/mL and 0.75 g/mL;
    (b) a pore volume of between 0.1 mL/g and 1.5 mL/g;
    (c) a particle distribution size of between 25 μm and 800 μm; or
    (d) an approximate water content of between 0.01 w/w and 9% w/w.

17. The method of claim 12, wherein the isoprenoid composition is exposed to the resin with a minimum residence time on the resin of at least 10 min with a maximum downflow superficial velocity of between 1 cm/min and 15 cm/min, and a maximum upflow superficial velocity of between 0.1 cm/min and 10 cm/min.

18. The method of claim 12, wherein the steps (a) through (c) are repeated from 2 to 20 times.

19. The method of claim 12, wherein the resin is regenerated following the collection of the isoprenoid from the resin in step (c).

20. The method of claim 19, wherein the resin is regenerated by:
    (e) adding a polar solvent to the resin;
    (f) removing the polar solvent from the resin;
    (g) heating the resin; and
    (h) cooling the resin.

21. The method of claim 12, wherein the isoprenoid is abietadiene, amorphadiene, cadinane, carene, cuminaldehyde, eugenol, farnesene, geranial, isoprene, limonene, myrcene, ocimene, α-pinene, β-pinene, sabinene, γ-terpinene, terpinolene, thujone, neral, eucalyptol, citronellal, carvone, or valencene.

22. The method of claim 12, wherein the isoprenoid is cadinane.

23. The method of claim 12, wherein the isoprenoid is farnesene.

24. The method of claim 12, wherein the isoprenoid is purified from the isoprenoid composition with a purity of from about 95% (w/w) to about 100% (w/w).

* * * * *